United States Patent
Frigg

(10) Patent No.: US 9,265,616 B2
(45) Date of Patent: Feb. 23, 2016

(54) EXPANDABLE IMPLANT

(75) Inventor: Robert Frigg, Langendorf (CH)

(73) Assignee: DePuy Synthes Products, Inc., Raynham, MA (US)

( * ) Notice: Subject to any disclaimer, the term of this patent is extended or adjusted under 35 U.S.C. 154(b) by 344 days.

(21) Appl. No.: 12/956,367

(22) Filed: Nov. 30, 2010

(65) Prior Publication Data

US 2012/0041557 A1 Feb. 16, 2012

Related U.S. Application Data

(60) Provisional application No. 61/372,219, filed on Aug. 10, 2010, provisional application No. 61/372,245, filed on Aug. 10, 2010.

(51) Int. Cl.
| | | |
|---|---|---|
| *A61F 2/44* | (2006.01) | |
| *A61B 17/68* | (2006.01) | |
| *A61B 17/88* | (2006.01) | |
| *A61F 2/46* | (2006.01) | |
| *A61L 27/46* | (2006.01) | |
| *A61L 27/50* | (2006.01) | |
| *A61B 17/80* | (2006.01) | |
| *A61F 2/30* | (2006.01) | |

(52) U.S. Cl.
CPC ............... *A61F 2/441* (2013.01); *A61B 17/686* (2013.01); *A61B 17/8855* (2013.01); *A61F 2/4611* (2013.01); *A61L 27/46* (2013.01); *A61L 27/50* (2013.01); *A61B 17/809* (2013.01); *A61F 2/30767* (2013.01); *A61F 2002/3092* (2013.01); *A61F 2002/30579* (2013.01); *A61F 2002/30584* (2013.01); *A61F 2002/30586* (2013.01); *A61F 2002/30668* (2013.01); *A61F 2002/465* (2013.01); *A61F 2002/4629* (2013.01); *A61F 2310/00796* (2013.01); *A61L 2430/02* (2013.01)

(58) Field of Classification Search
CPC ....... A61F 2/441; A61F 2/442; A61F 2/4611; A61F 2/0013; A61F 2/002; A61F 2002/30586; A61F 2002/501; A61F 2002/5012; A61F 2002/5032; A61F 2250/0003
USPC ............................................ 623/17.11–17.12
See application file for complete search history.

(56) References Cited

U.S. PATENT DOCUMENTS

| | | | |
|---|---|---|---|
| 5,972,015 A | 10/1999 | Scribner et al. | |
| 7,294,187 B2 | 11/2007 | Chow et al. | |
| 2004/0186576 A1* | 9/2004 | Biscup et al. .............. | 623/17.12 |
| 2004/0230309 A1 | 11/2004 | DiMauro et al. | |
| 2005/0090901 A1* | 4/2005 | Studer ......................... | 623/17.12 |
| 2005/0234453 A1 | 10/2005 | Shaolian et al. | |
| 2006/0064170 A1 | 3/2006 | Smith et al. | |
| 2006/0229628 A1* | 10/2006 | Truckai et al. ................. | 606/90 |

(Continued)

FOREIGN PATENT DOCUMENTS

| | | |
|---|---|---|
| EP | 1421921 | 5/2004 |
| WO | WO2004/016205 A2 | 2/2004 |
| WO | WO 2008/079864 | 7/2008 |
| WO | WO2009/013752 A2 | 1/2009 |
| WO | WO2011/066522 A2 | 6/2011 |

*Primary Examiner* — Christopher D Prone
(74) *Attorney, Agent, or Firm* — Baker & Hostetler LLP

(57) ABSTRACT

An expandable portion of an implant has a total volume and includes a plurality of chambers, each having a volume less than the total volume. At least one of the chambers includes a biocompatible media which is liquid at room temperature. The at least one chamber is closed, so that by increasing the temperature of the liquid, the pressure in the chamber increases.

23 Claims, 20 Drawing Sheets

(56) References Cited

U.S. PATENT DOCUMENTS

| | | |
|---|---|---|
| 2006/0241768 A1 | 10/2006 | Trieu |
| 2006/0282166 A1 | 12/2006 | Molz et al. |
| 2007/0233250 A1* | 10/2007 | Shadduck .................. 623/17.11 |
| 2007/0270953 A1 | 11/2007 | Trieu |
| 2008/0269745 A1 | 10/2008 | Justin |
| 2009/0024161 A1 | 1/2009 | Bonutti et al. |
| 2011/0160870 A1 | 6/2011 | Baumgartner |

* cited by examiner

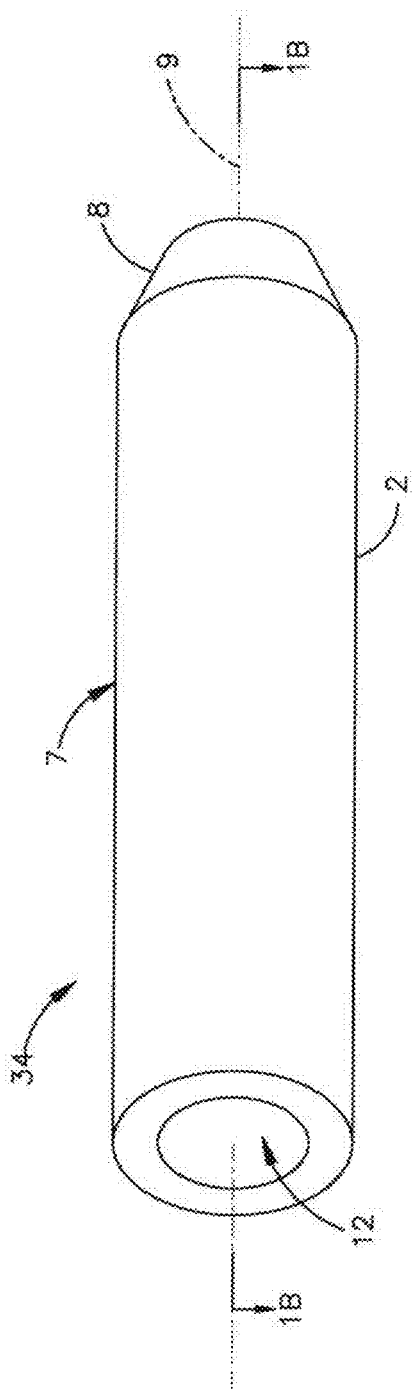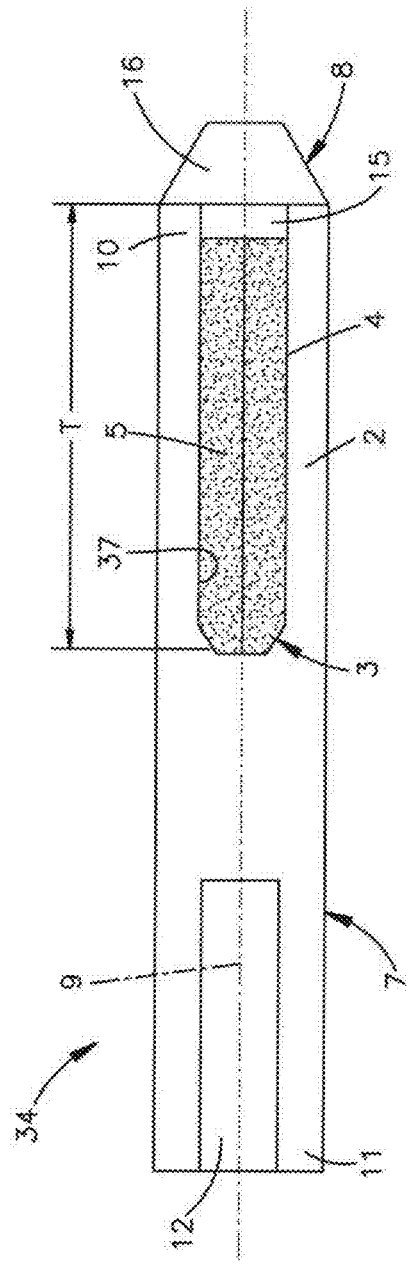
Fig.1A
Fig.1B

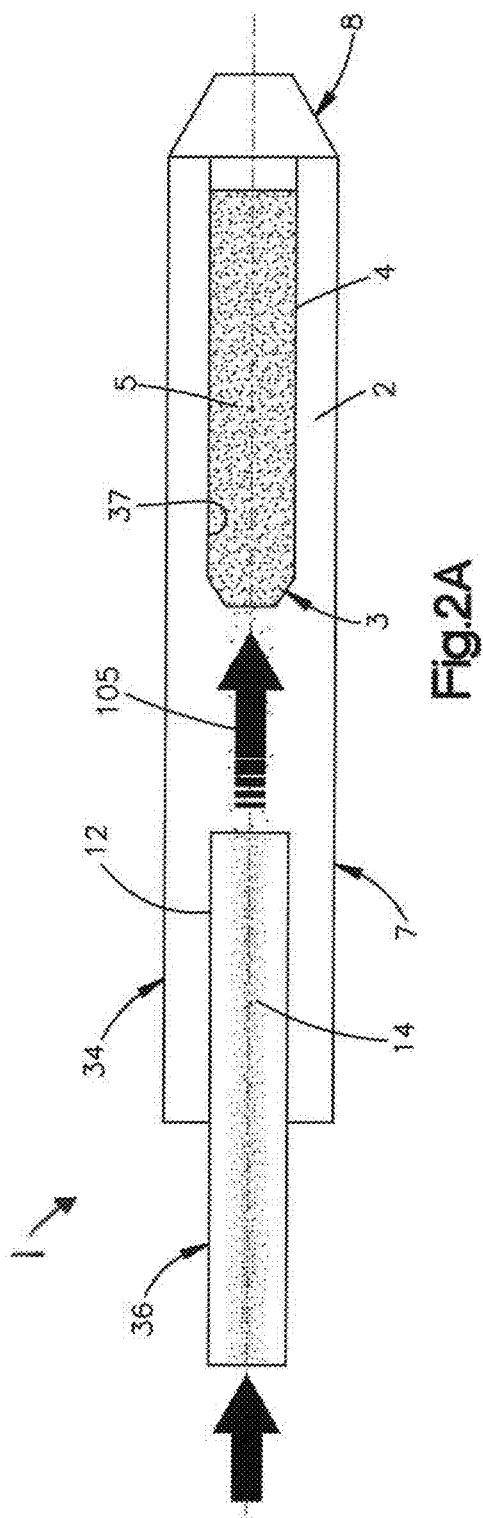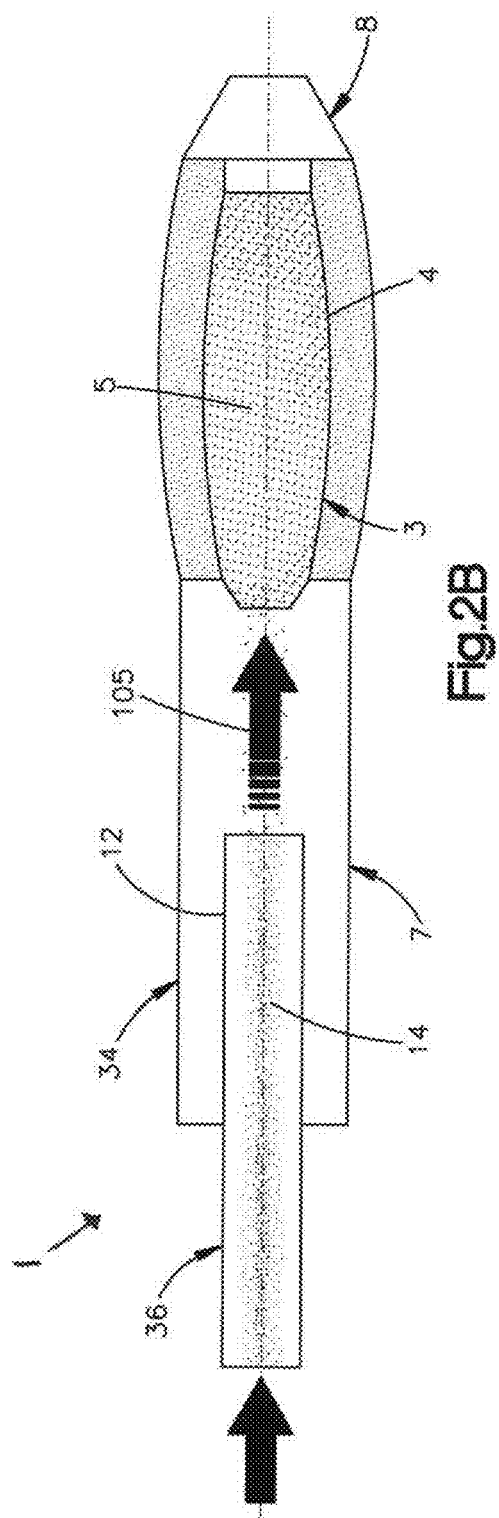

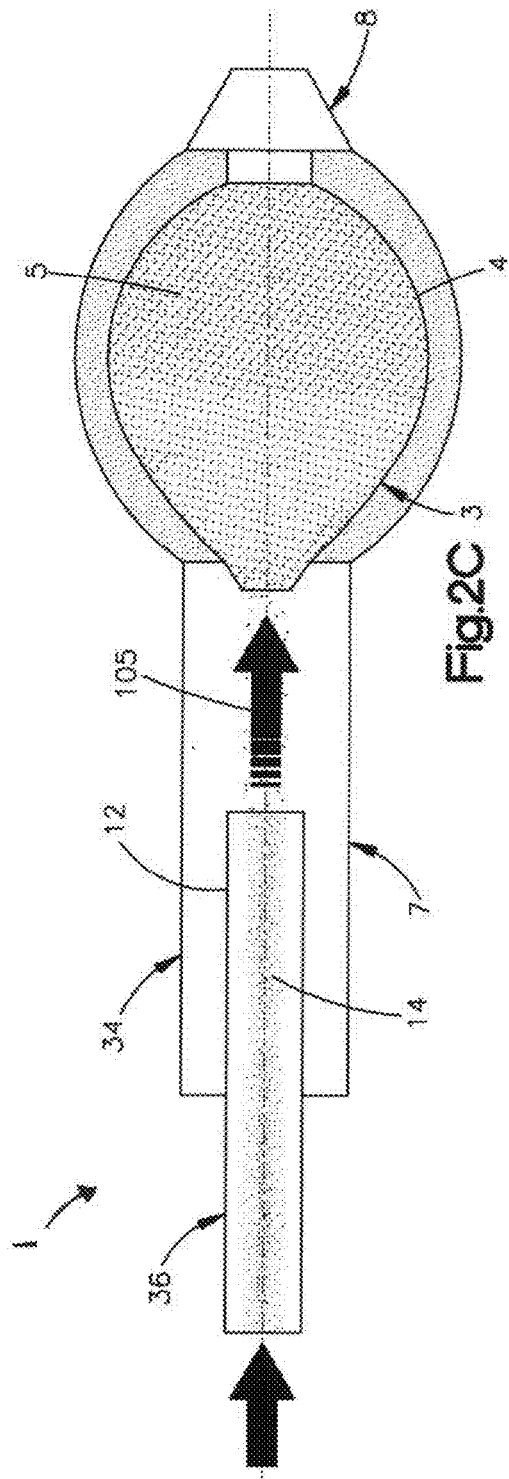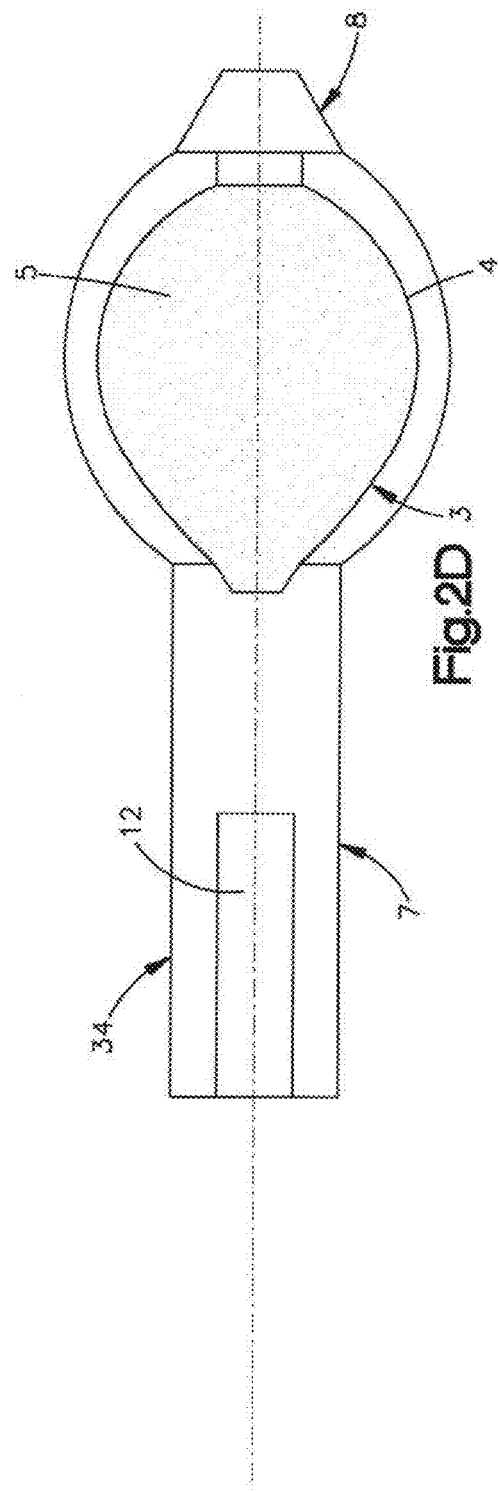

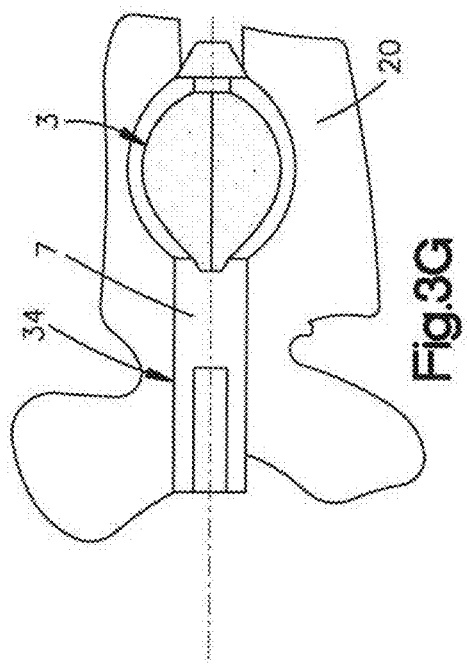
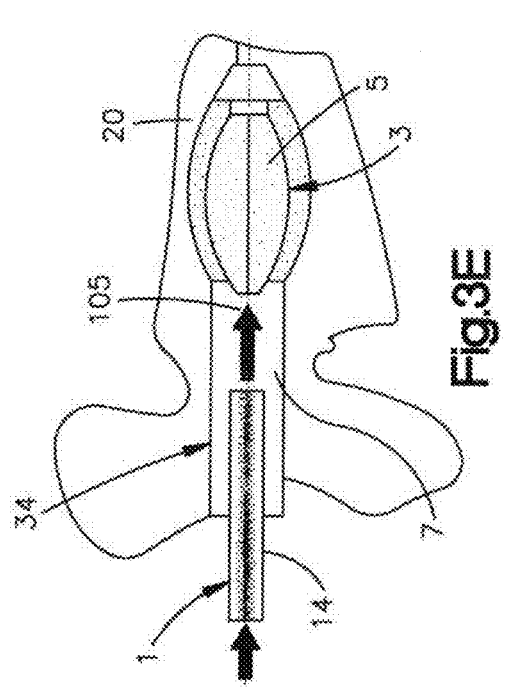
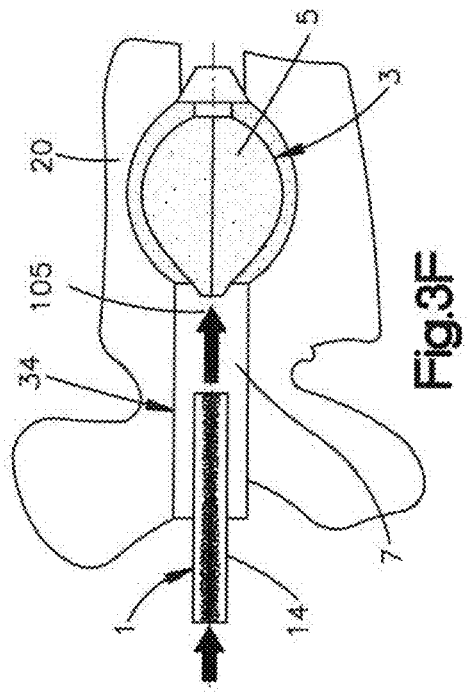

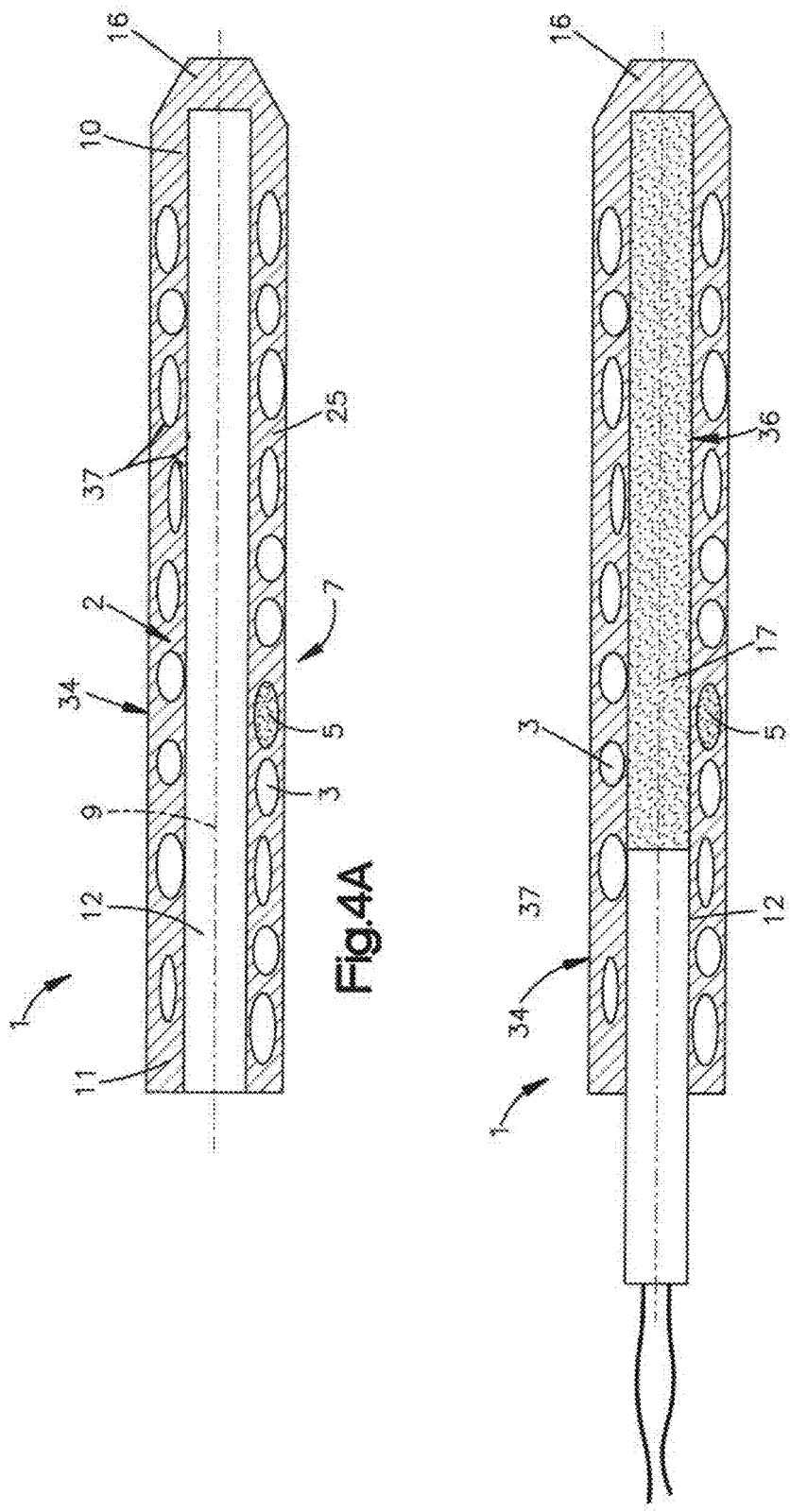

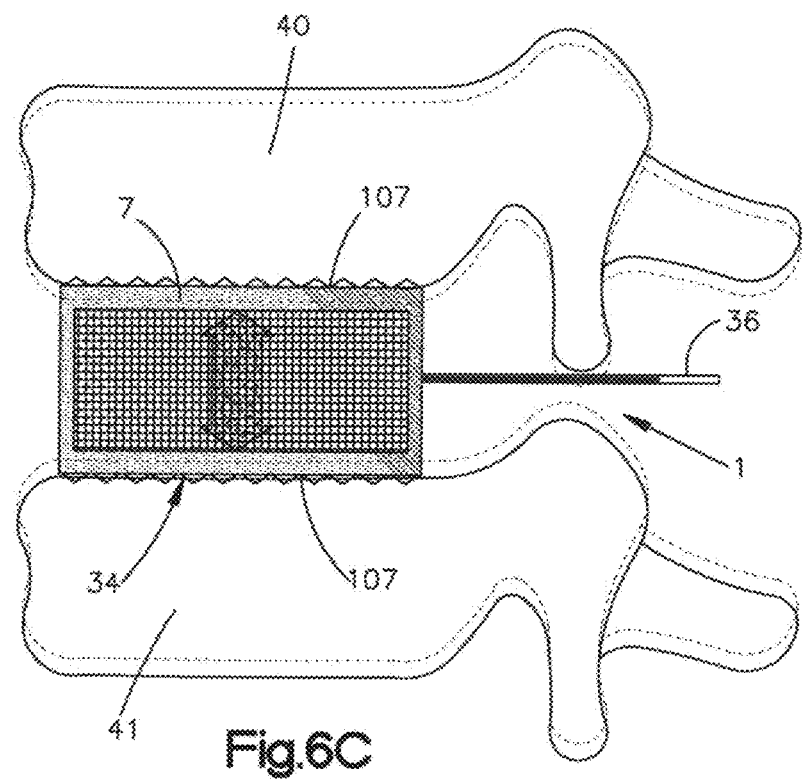
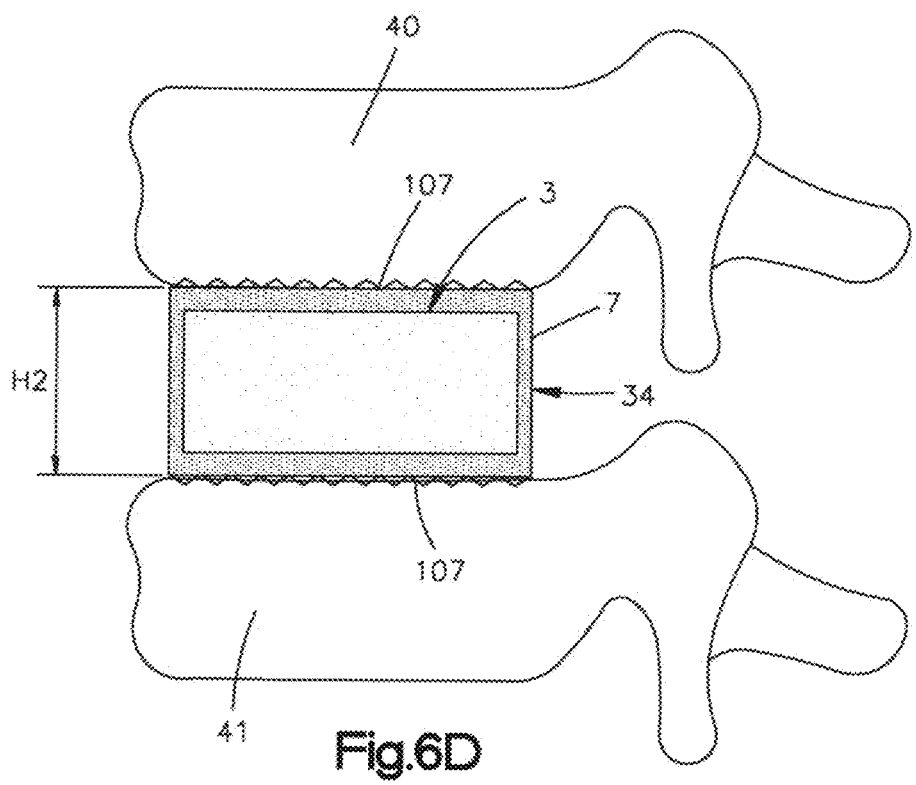

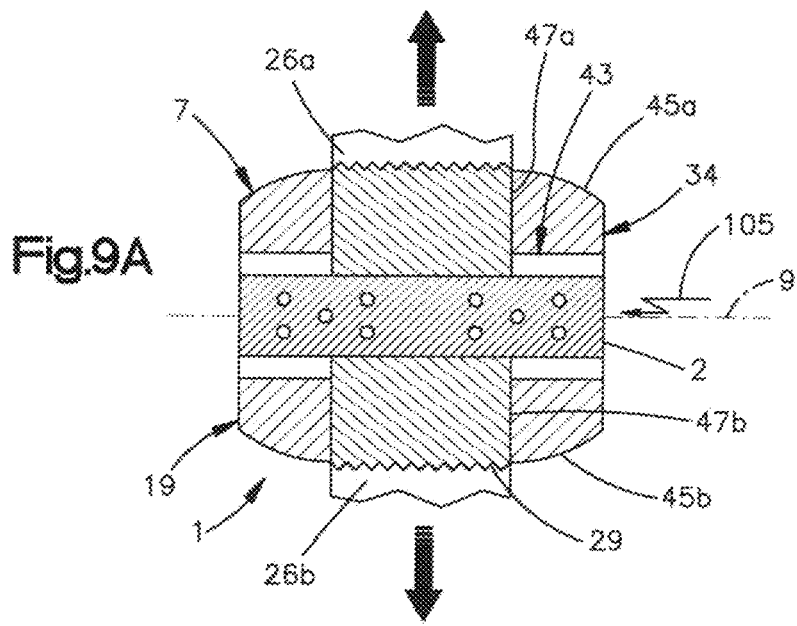
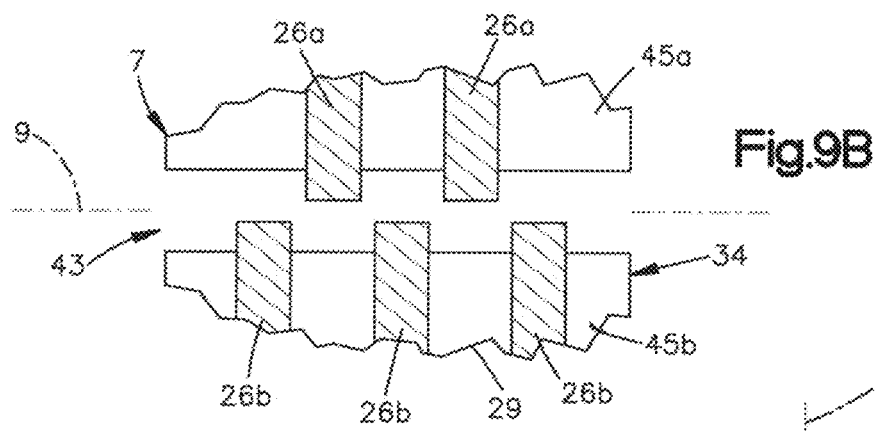
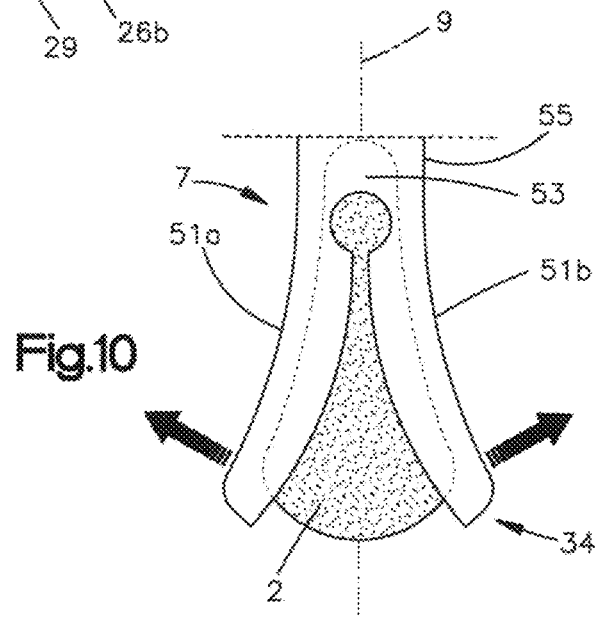

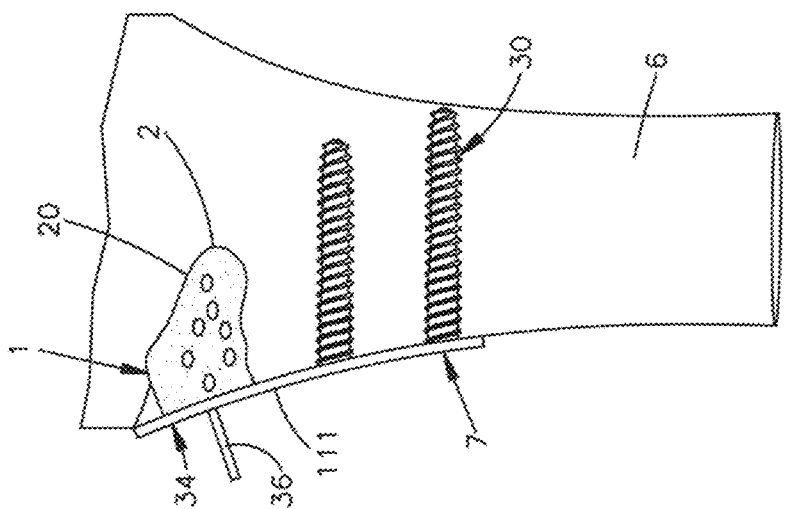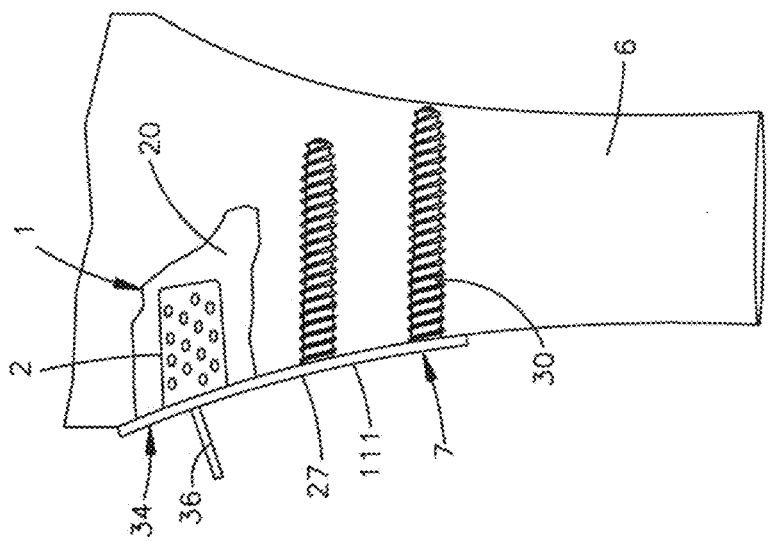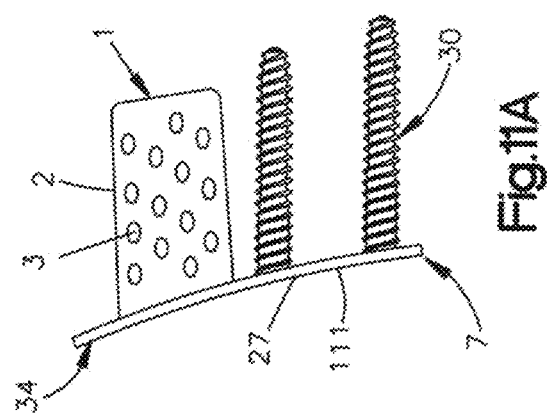

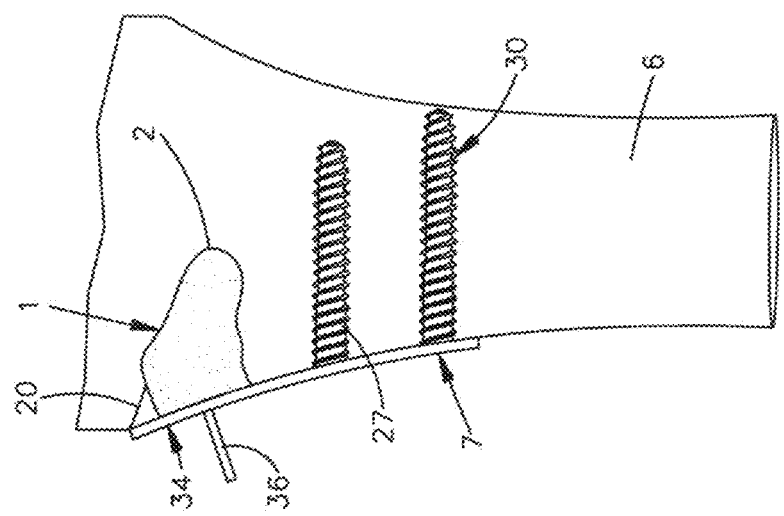
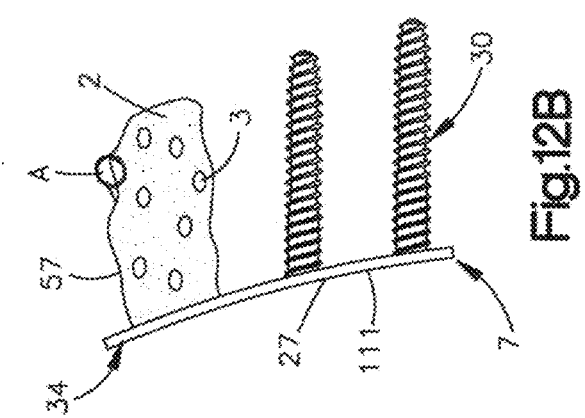
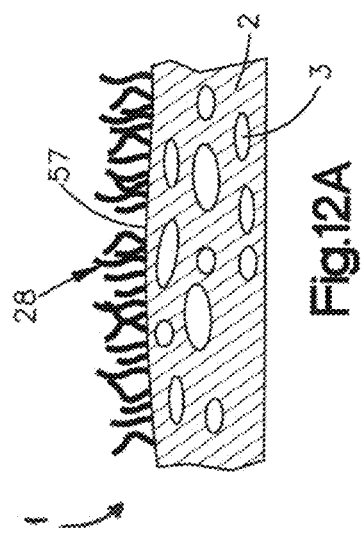

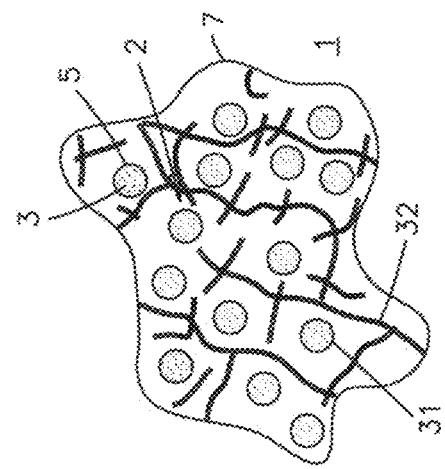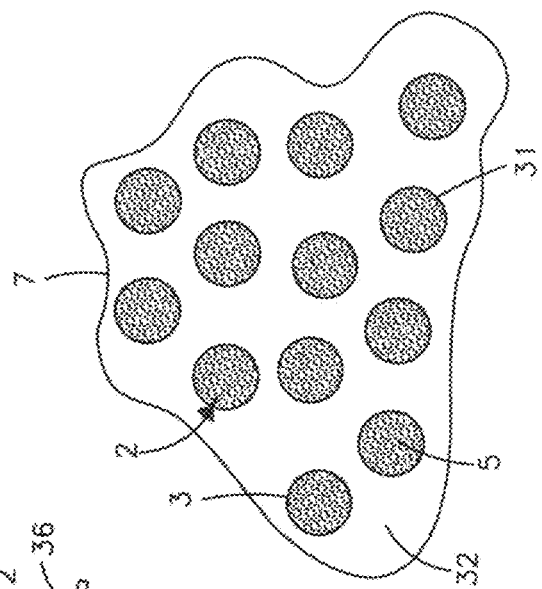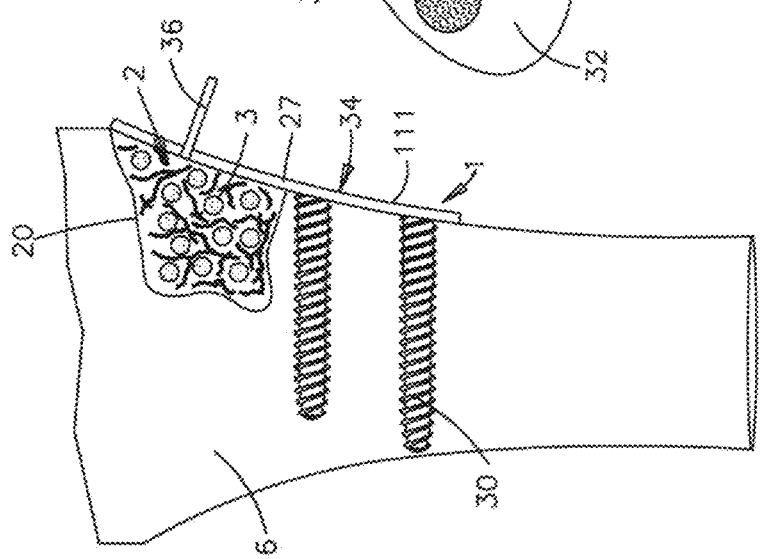

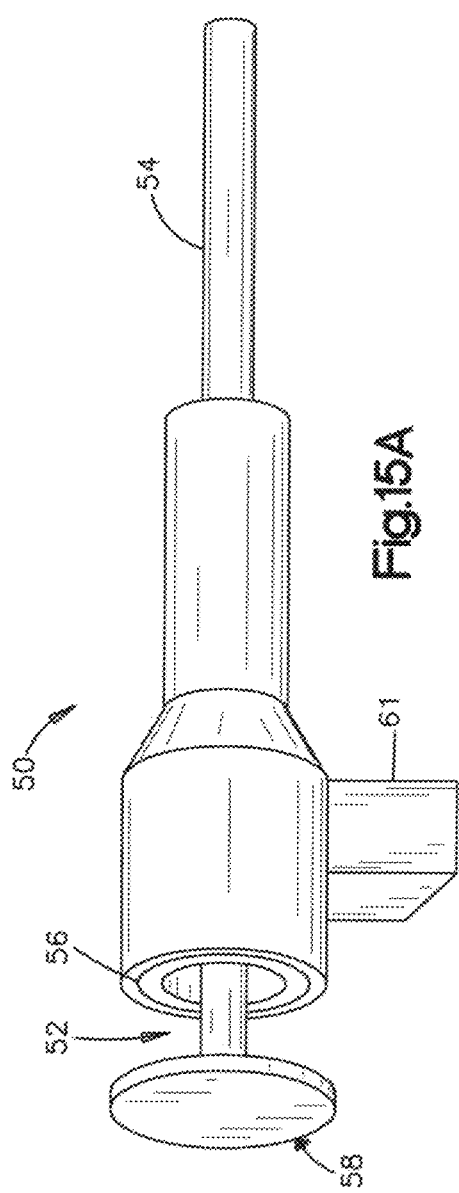
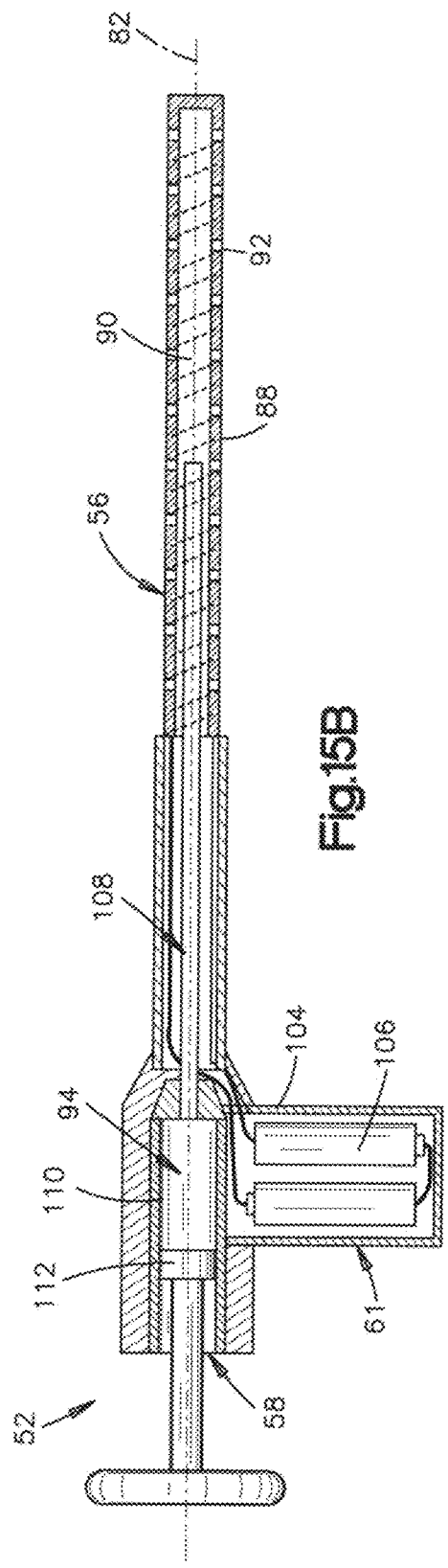

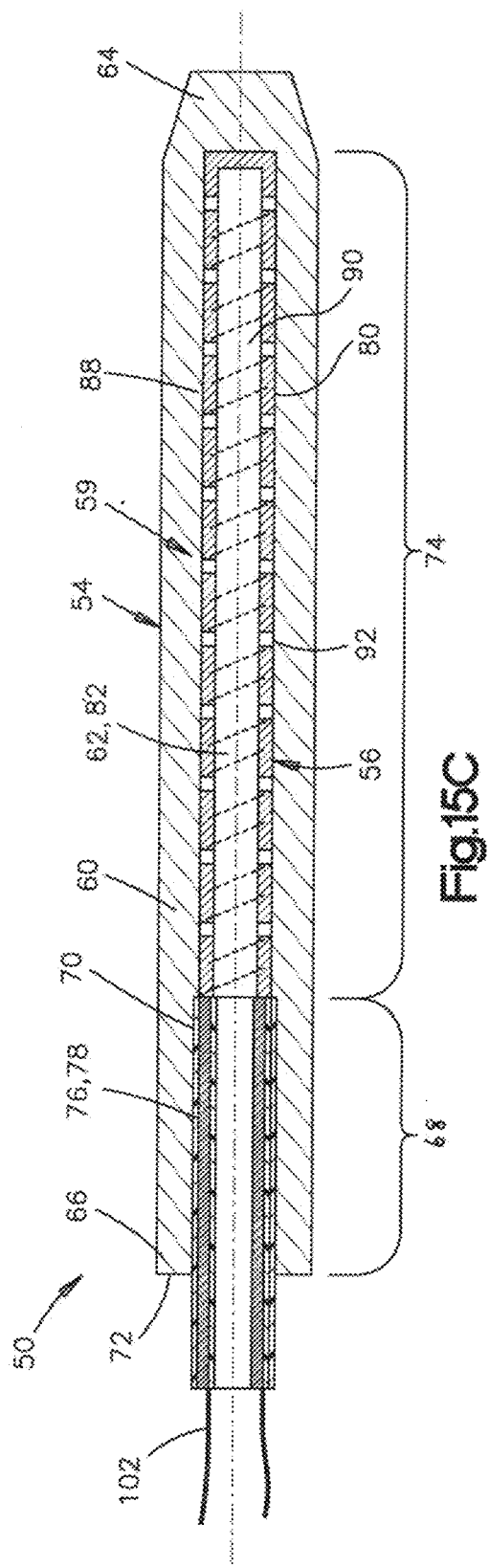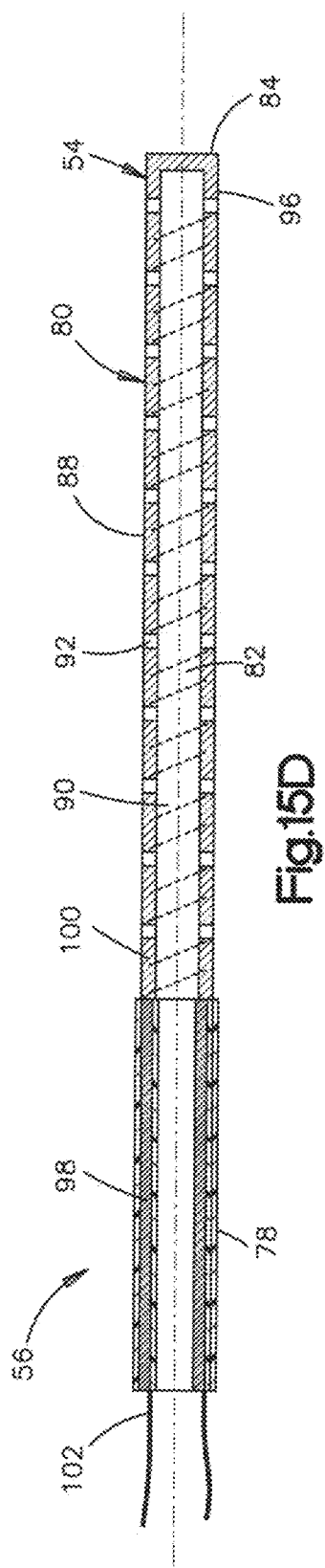

EXPANDABLE IMPLANT

CROSS-REFERENCE TO RELATED APPLICATIONS

This application claims priority to U.S. Provisional Application Ser. No. 61/372,219 filed Aug. 10, 2010, and further claims priority to U.S. Provisional Application Ser. No. 61/372,245, filed Aug. 10, 2010, the disclosure of each of which is hereby incorporated by reference as if set forth in its entirety herein.

FIELD OF THE DISCLOSURE

The present disclosure generally relates to a polymeric material and to an implant having at least a portion that includes the polymeric material and which has the form of a surgical implant or instrument the shape of which can be changed after implantation. More particularly, the present disclosure relates to an implant system including the implant having one or more closed chambers containing a biocompatible liquid, and to an energy emitter configured to fix the implant in a bone. More particularly still, the present disclosure relates to a method of using the implant and the implant system.

BACKGROUND

Bone fixation devices made of polymeric materials are today commonly used as pins, screws or pegs. One clinical problem encountered is that the pullout strength of these devices is quite low. To increase the holding strength, welding, e.g. by heat introduction of these polymeric implants is used. Depending on the anatomical shape or density of the bone, welding may not sufficiently increase the holding strength. Another clinical problem can arise due to thin or weak bone structures.

SUMMARY

An implant is configured to expand its volume after implantation into a target anatomical location.

In accordance with one embodiment, the implant is expandable by the action of energy transmitted through the implant body and heating up an encapsulated liquid pre-introduced in the implant.

The pressure of vapour (when a liquid passes from its liquid state to its gaseous state) exerts the expansive force onto the implant body, thereby changing the shape of the implant body, an expandable portion of which or all of which can be polymeric. The vapour is generated by heating a small amount of liquid, e.g. water or a saline solution pre-introduced in to at least one chamber that is disposed in the implant body. Any suitable heating source can be used to heat the encapsulated liquid. The degree of heating (temperature and duration) can depend, for instance, on the type of polymer (glass transition temperature), and the size and distribution of the chambers. The necrotic temperature need not be reached.

The polymeric material of the implant body according to one embodiment has a total volume and comprises a plurality of chambers each having a volume, such that the aggregate volume of the chambers is less than the total volume of the implant body. At least one of the chambers contains a biocompatible media which is liquid at a first temperature, e.g., room temperature. The at least one chamber is closed, so that by increasing the temperature of the liquid the pressure in the chamber increases.

Accordingly, a dramatic increase in pressure is achieved in the chambers when the liquid in the chambers passes from its liquid state to its gaseous state allowing a considerable expansive force to be exerted onto the polymeric implant body.

In one embodiment, the polymeric material is mixed with a bone-like substance, such as calcium phosphates or apatites.

In another embodiment the polymeric material is used as a substrate or core material for a bone-like substance, such as calcium phosphates or apatites.

In accordance with another embodiment, the implant can further include an energy absorbing member that is configured to soften at least part of the polymeric material of the implant body, increase the temperature of the liquid contained in the chamber, and thereby the vapour pressure in the at least one chamber, and thereby expanding the total volume of the implant body by the action of the vapour pressure on the softened polymeric material.

In another embodiment of the implant the polymeric material is transparent.

In a further embodiment the implant further includes an energy emitter configured to soften at least part of the polymeric material, increase the temperature of the liquid and thereby the vapour pressure in the at least one chamber and thereby expanding the total volume of the implant body by the action of the vapour pressure on the softened polymeric material.

In again another embodiment of the implant the biocompatible liquid is a composition based on polar molecules, preferably liquid water or an aqueous solution. The biocompatible liquid can have a boiling point—as measured at normal pressure—of at most 100° C.

In yet another embodiment of the implant the energy absorbing member is a chromophore.

In a further embodiment of the implant the biocompatible liquid is colored and is thereby provided as an energy receiver or absorber.

In still a further embodiment of the implant the energy absorbing member is placed at the inner surface of the at least one chamber.

In again a further embodiment of the implant the polymeric material of an expandable portion of the implant body is able to absorb energy.

In another embodiment of the implant the at least one chamber has a volume smaller than 100 mm$^3$, preferably smaller than 1 mm$^3$.

In yet another embodiment of the implant the ratio between the total volume of the implant body or the expandable portion of the implant body and the sum of the volumes of the chambers is in the range of 2:1 to 5:1.

In again another embodiment of the implant the at least one chamber is not interconnected with any of the other chambers.

In a further embodiment of the implant the at least one chamber has a minimal distance to the surface of the implant body of 0.1 mm, preferably of 0.2 mm.

In still a further embodiment of the implant the polymeric material is polymethylmethacrylate.

In yet a further embodiment of the implant the at least one chamber is completely filled with the biocompatible liquid.

In another embodiment of the implant the at least one chamber is only partly filled with the biocompatible liquid, preferably to less than 50%.

In a further embodiment the implant further comprises a valve coupled between the at least one chamber and the internal surface of the implant body, such that the energy emitter can be press-fit into a cavity of the implant body, and if a maximal desired pressure is reached in the at least one chamber during energy emission, the pressure is released through the valve and against the energy emitter so as to push the energy emitter out of the implant and release the excess pressure.

In again a further embodiment of the implant the portion made of a polymeric material is arranged in an outer layer surrounding an inner core having no chambers. This configuration provides enhanced stability of the implant.

In yet a further embodiment of the implant the portion made of a polymeric material is arranged in an inner hollow space that is encompassed by one or more expandable parts.

In still a further embodiment of the implant the portion made of a polymeric material comprises chambers embedded in a spongy material with open pores.

In another embodiment the implant includes a bone plate portion, and the portion made of a polymeric material can be fixed to the bone plate portion.

In again another embodiment of the implant the portion made of a polymeric material can have a surface including a macroscopic three-dimensional structure.

In a further embodiment the implant is made of a stiff material.

In accordance with another aspect, a method is provided for fixing surgical implants into bone using the implant and comprising the following steps:

inserting the implant in its unexpanded state into a cavity in a bone;
supplying energy to the portion of the implant which is made of the polymeric material; and
increasing the temperature of the liquid and thereby the vapour pressure in the one or more chambers by supplying energy emitted by the energy emitter until the implant achieves its expanded state.

In accordance with another aspect, a method is provided for augmenting bones using the material, comprising the following steps:

producing a cavity in bone;
inserting the expandable portion in its unexpanded state into the cavity; and
increasing the temperature of the liquid and thereby the vapour pressure in the one or more chambers of the polymeric material by supplying energy emitted by an energy emitter until the polymeric material achieves its expanded state.

In accordance with another embodiment, the present disclosure is related to a kit for bone fixation, and components of the kit. The kit can include an implant that includes a polymeric implant body which, in turn, defines an internal chamber, and an expansion assembly that can be coupled to the implant. The expansion assembly includes an expansion device that is configured to be coupled to the implant, and an injection device configured to inject a biocompatible fluid (e.g., liquid or vapor) into the chamber. The chamber defines an open end, and the expansion device is configured to be coupled to the implant in a fluid tight manner, so as to provide a fluid tight seal therebetween.

The expansion device can include any suitable heating member configured to heat the implant. The degree of heating (temperature and duration) can depend, for instance, on the type of polymer (glass transition temperature) of the implant. The heat is desirably applied at a level that does not create bone necrosis by excessive induced heat.

In accordance with one embodiment, the polymer is heated to its glass transition temperature. Additionally, the injected biocompatible fluid is heated to this gas transition temperature as the polymer is heated to its glass transition temperature. Accordingly, the biocompatible fluid injected into the chamber is vaporized, and exerts a significant expansion force onto the implant. Because the polymer has been heated to its glass transition temperature, the expansion force causes the implant to expand. Thus, the implant can be provided in a first or initial state, and can be expanded to a second or expanded state from the first state. The implant has a greater volume in the second state than in the first state, which can be an unexpanded state or partially expanded state. Further, the expansion device can have a simple configuration.

In another embodiment, the chamber has an entrance section with an orifice at an outer surface of the implant and an expandable portion configured as a pocket.

In another embodiment, the chamber has an inner peripheral wall and the expansion device does not contact the peripheral wall of the chamber in the range of the expandable portion.

In another embodiment, the expansion device includes a sleeve that defines a central opening, and one or more radial perforations that extend through the sleeve. The perforations can be distributed as desired, such as over a length of the sleeve that corresponds to the length of the expandable portion of the chamber in the implant.

In another embodiment, the expansion device is releasably fixable or coupled to the implant via complementary engagement members.

In a further embodiment, the engagement members are provided as an outer thread which is engageable with an inner thread in the entrance section of the chamber.

In a further embodiment, the engagement members can define a snap-lock, a bayonet lock or a Luer-lock so as to releasably couple the expansion device to the implant in a fluid tight manner.

In yet a further embodiment, the expansion device includes a heating member, such as an electric resistance heating member.

In still a further embodiment, the expandable portion has a cross-sectional area which is greater than the cross-sectional area of the entrance section when the implant is in an unexpanded state.

In another embodiment, the expandable portion has a prismatic shape, such as a substantially cuboidal shape.

In yet another embodiment, implant has an outer wall that is concavely curved when the implant is in an unexpanded state, such that the outer wall is configured to bulge outward when the implant is expanded.

In again another embodiment, the expansion device includes a handle that has a power supply which is electrically connectable to the heating member.

In a further embodiment, the injection device includes a cylinder and a piston suitable to inject a biocompatible liquid from the cylinder into the central opening of the sleeve. The injection device can further include a cannula arranged in fluid communication with the cylinder and the piston and which is insertable into the central opening of the sleeve.

In again a further embodiment, the polymeric material can be polymethylmethacrylate or poly-L-lactide (PLLA).

According to a further aspect, an expansion assembly is configured to expand an implant, the expansion assembly including an expansion device and an injection device. The expansion device includes a sleeve that is insertable into a chamber of the implant and having a central opening and a plurality of radial perforations that extend through the sleeve. The injection device can be coupled to the sleeve is configured to inject a biocompatible fluid (e.g., liquid or vapor) into the central opening of the sleeve. The injection device includes a fluid-containing cylinder and a piston suitable to inject a biocompatible liquid from the cylinder into the central opening of the sleeve.

The piston can be manually driven by a surgeon so that a tactile control of the pressure in the chamber of an implant is possible.

In another embodiment, an outer thread of the expansion device is engageable with an inner thread of the implant.

In another embodiment, the sleeve is releasably fixable to the implant in a fluid tight manner via a snap-lock, a bayonet lock or a Luer-lock.

In another embodiment, the expansion device includes a heating member, such as an electric resistance heating member. Accordingly, in addition to applying heat to the implant, a liquid injected into the central opening of the sleeve can be heated or evaporated when injected through the central opening and into the radial perforations of the sleeve. The heating or vaporization of the fluid causes additional pressure to amass in the chamber of the implant, thereby providing a force that biases the implant to expand outward.

In yet another embodiment, the expansion device includes a handle that has a power supply which is electrically connectable to the heating member.

In a further embodiment, the injection device includes a cannula arranged in fluid communication with the cylinder and the piston, and which is insertable into the central opening of the sleeve. The cannula allows the injected biocompatible fluid to be substantially homogenously heated in the central opening of the sleeve.

In accordance with another aspect, the implant includes an implant body made from a polymeric material. The expansion assembly is configured to expand the implant body from an unexpanded state to expanded state.

In accordance with yet another aspect, a method is provided for fixing a surgical implant in a bone. The method comprising the steps of:

inserting an implant into a hole in a bone; the implant having a chamber;
    heating the implant until the implant is softened and plastically deformable;
    coupling an expansion assembly to the implant in a fluid tight manner; and
    injecting a biocompatible fluid from the expansion device into the chamber of the implant.

Heating the implant and injecting the biocompatible fluid allows the implant body to expand as desired. Further, the kit can have a simple configuration.

In another embodiment, the implant is made from a polymeric material, such as polymethylmethacrylate.

In another embodiment, the implant is heated to a temperature of 40 to 200° C., preferably of 100 to 160° C., such as 150° C.

In a further embodiment, the implant is expanded via fluid force (e.g., hydraulic or pneumatic force) only.

In again a further embodiment of the method the chamber has an entrance section with an orifice at an outer surface of the implant and wherein the expansion device does not contact the peripheral wall of the chamber beyond the entrance section.

In another embodiment, the chamber has an entrance section with an orifice at an outer surface of the implant and wherein the entrance section of the chamber comprises an inner thread.

In another embodiment, the expansion device includes an outer thread that is engageable with the inner thread in the entrance section of the chamber so as to couple the expansion device to the implant.

In yet another embodiment, the expansion device is releasably fixed to the implant via complementary engagement members, such as the above-described threads.

In still another embodiment, the engagement members provide a snap-lock, a bayonet lock or a Luer-lock.

BRIEF DESCRIPTION OF THE DRAWINGS

The foregoing summary, as well as the following detailed description of preferred embodiments of the application, will be better understood when read in conjunction with the appended drawings. For the purposes of illustrating the embodiments of the present application, there is shown in the drawings preferred embodiments. It should be understood, however, that the application is not limited to the precise arrangements and instrumentalities shown. In the drawings:

FIG. 1A is a perspective view of an expandable implant constructed in accordance with one embodiment, illustrated in an unexpanded configuration;

FIG. 1B is a sectional side elevation view of the implant illustrated in FIG. 1B, taken along line 1B-1B, showing an implant body that defines a chamber;

FIG. 2A is a sectional side elevation view of an implant system including the expandable implant illustrated in FIG. 1B and an energy emitter coupled to the implant, the energy emitter configured to emits energy to an expansion fluid disposed in the chamber;

FIG. 2B is a sectional side elevation view of the implant system illustrated in FIG. 2A, but showing a portion of the expansion fluid vaporized such that the implant is in an expanded configuration;

FIG. 2C is a sectional side elevation view of the implant system illustrated in FIG. 2B, but showing a greater portion up to all of the expansion fluid vaporized such that the implant in a fully expanded configuration;

FIG. 2D is a sectional side elevation view through the implant illustrated in FIG. 2C after the energy emitter has been removed;

FIG. 3E is a sectional side elevation view similar to FIG. 3D, but showing the implant in a more expanded configuration;

FIG. 3F is a sectional side elevation view similar to FIG. 3E, but showing the implant in a fully expanded configuration;

FIG. 3G is a sectional side elevation view similar to FIG. 3F, but showing the implant with the electromagnetic radiation emitter removed.

FIG. 4A is a sectional side elevation view of an expandable implant similar to the expandable implant illustrated in FIG. 1B, but having a plurality of chambers in accordance with another embodiment;

FIG. 4B is a sectional side elevation view of an implant system including the expandable implant illustrated in FIG. 4A and an energy emitter coupled to the implant, the energy emitter configured to emits energy to an expansion fluid disposed in the chambers;

FIG. 6C is a side elevation view of the implant system illustrated in FIG. 6B, showing the implant in the expanded configuration, FIG. 6D is a side elevation view of the implant illustrated in FIG. 6C, whereby the energy emitter has been removed from the implant;

FIG. 9A is a sectional side elevation view of an expandable implant constructed in accordance with another embodiment;

FIG. 9B is a sectional side elevation view of an expandable implant similar to FIG. 9A, but having a plurality of upper and lower slider members constructed in accordance with another embodiment;

FIG. 10 is a sectional side elevation view of an expandable implant illustrated as a dowel in accordance with another embodiment;

FIG. 11A is a side elevation view of an implant system including an expandable implant illustrated as a bone fixation plate, showing the implant in an unexpanded configuration;

FIG. 11B is a side elevation view of the implant system illustrated in FIG. 28A implanted in an underlying bone;

FIG. 11C is a side elevation view of the implant system illustrated in FIG. 28B, showing the implant in an expanded configuration;

FIG. 12A is an enlarged sectional side elevation view of Region A illustrated in FIG. 12B;

FIG. 12B is a side elevation view of an implant system including an expandable implant having a bone growth region indicated at Region A;

FIG. 12C is a side elevation view of the implant system illustrated in FIG. 12A, shown implanted into an underlying bone and subsequently expanded;

FIG. 14A is a sectional side elevation view of an implant assembly including an expandable implant having a plurality of chambers defined by a PLLA envelope embedded in a porous wrapping;

FIG. 14B is a sectional side elevation view of an expandable portion of the implant illustrated in FIG. 14A;

FIG. 14C is a schematic sectional side elevation view of the expandable portion of the implant illustrated in FIG. 14B;

FIG. 15A is a perspective view of an implant system constructed in accordance with an alternative embodiment, including an expandable implant and an expansion assembly that includes an expansion device, an injection device, and an energy emitter;

FIG. 15B is a sectional side elevation view of the implant system illustrated in FIG. 15A;

FIG. 15C is an enlarged sectional side elevation view of the expandable implant and the expansion device illustrated in FIG. 15A;

FIG. 15D is a sectional side elevation view of the expansion device illustrated in FIG. 15C;

DETAILED DESCRIPTION

Figure 3C:
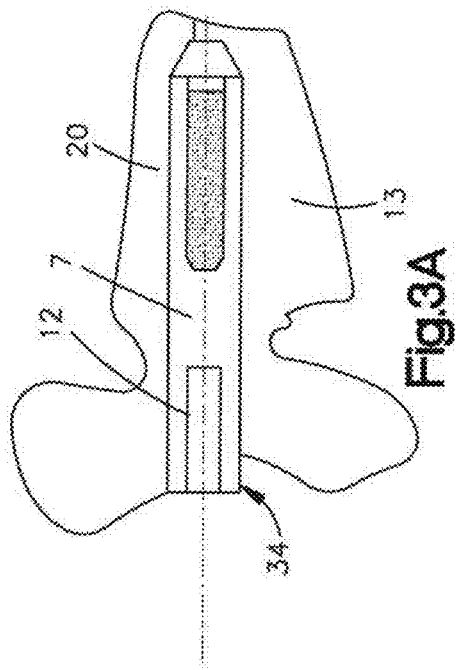
FIG. 3C is a sectional side elevation view similar to FIG. 3B, but showing the electromagnetic radiation emitter in an energized state.
Figure 3D:
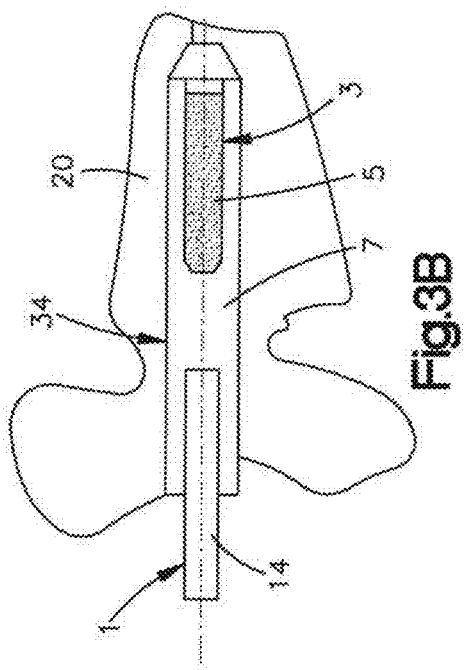
FIG. 3D is a sectional side elevation view similar to FIG. 3C, but showing the implant in a partially expanded configuration.
Figure 3A:
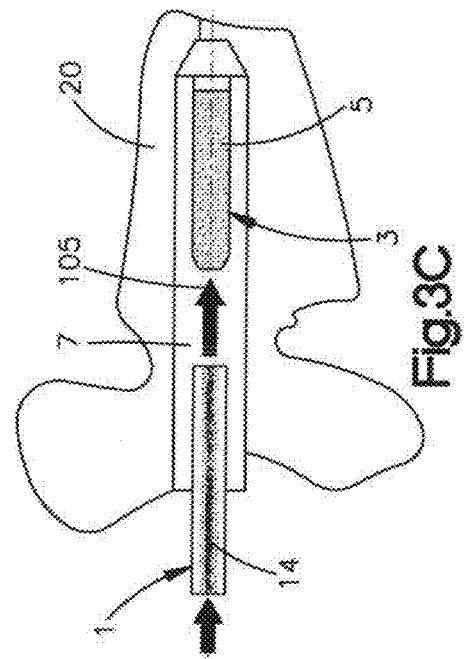
FIG. 3A is a sectional side elevation view of the implant inserted into a damaged vertebral body.

Definitions of terms frequently used in the following description:

Photoconductor: The term photoconductor as used herein refers to a flexible or rigid optical light-conducting structure, such as for instance a glass fiber cable, a reflecting hose (e.g. also nano-tube) that conducts lights and usable to transmit electromagnetic radiation from a source to an implant body 7. In order to conduct the light through the photoconductor in the implant body 7 up to the desired point, the photoconductor in the implant may on one hand actually conduct the light, meaning for instance to the tip of a pin and then distribute it there, so as to reach the inner surface of a chamber 3, for instance by diffusion.

Light source: A light source as used herein refers to any source of electromagnetic radiation, such as an incandescent light bulb, a vapor emission lamp, a diode, a semiconductor, a spark, a flame, sunlight, and the like.

Laser: Lasers are preferred sources of energy, as they are typically emitting only a few narrowly defined frequencies of electromagnetic radiation. The absorption spectra of one chromophore (or several, up to many chromophores) of the non absorbing portion of the implant as well as of the body's surroundings may thus be tuned to each other. In a preferred application, the laser radiates in a preferably monochromatic frequency that is barely absorbed by the implant, strongly by the chromophore, and again only barely by the surroundings. This makes it possible to supply different areas with different chromophores in the implant, and to specifically heat them with the electromagnetic radiation frequency that may be required on a case-by-case basis.

Chromophore: The term chromophore as used herein refers to colors or pigments added to the polymer or coated on the polymer to absorb the electromagnetic radiation and convert it to heat. In one application, substances can be added to or coated onto the implant without having chromophore properties. However, while being introduced into the human body, these substances change upon contact with the human body, for instance as a reaction to the pH of body tissue, to body salts, body moisture or body temperature, and this discolors the substance and renders it absorbent for the electromagnetic radiation. Thus the area coming in contact with the body can warm up, because the implant discolors at that point. Examples of chromophores include chlorophyll, carbon black, graphite, fluorescein, methylene blue, indocyanine green, eosine; eosine Y (514 nm), ethyleosine (532 nm), acridine, acridine orange, copper phtalocyanine, chrome-cobalt-aluminum oxide, ferrous ammonium citrate, pyrogallol, logwood extract, chlorophyll-copper complex, D&C blue No. 9, D&C green No. 5, [phtalocyaninate(2-)] copper, D&C blue no. 2, D&C blue no. 6, D&C green no. 6, D&C violet no. 2, D&C yellow No. 10. Certain fluorescent chromophores do not absorb electromagnetic radiation under certain circumstances, but rather radiate light that is absorbed from the surroundings, the polymer or any additionally introduced chromophore.

Light-absorbing, non-colored polymer: Light-absorbing polymer as used herein refers to a polymer having a property of its own to absorb light of a certain wavelength, without the addition of chromophore. The polymer can be heated in advance to the point of discoloration and thus is capable of absorbing more light. The polymer can be partially carbonized or caramelized and thus light-absorbent.

Referring to FIGS. 1A-2D, an implant system 1 includes a bone fixation device or implant 34 and an energy emitter 36 configured to be operably coupled to the implant 34 so as to provide energy to the implant 34. The implant 34 includes an implant body 7 that is illustrated as elongate along a central longitudinal axis 9. The implant body 7 can be substantially cylindrical or prismatic, or define any suitable alternative geometric shape as desired. The implant body 7 defines a first or front end 10, and a second or rear end 11 that is longitudinally spaced from the front end 10 along the longitudinal axis 9. As used herein, the front end 10 can be referred to as disposed distal of the rear end 11, and the rear end 11 can be referred to as disposed proximal of the front end 10.

The implant body 7 defines an expandable portion 2 that is disposed at a location longitudinally distal of the rear end 11. The expandable portion 2 includes an internal surface 37 that in turn defines an outer perimeter of an internal chamber 3 that can be sized and shaped as desired. For instance, the chamber 3 can be substantially cylindrical or rectangular. The internal chamber 3 is configured to be filled with a biocompatible expansion fluid 5 which can be provided as, for instance, a normal saline solution. The chamber 3 is disposed proximate to the front end 10 of the implant body 7, and is open at its longitudinally front end. Thus, it can be said that the chamber 3 is open at the front end 10 of the implant body 7, and penetrates longitudinally into the implant body 7 to a depth T measured from the front end 10 towards the rear end 11. The biocompatible expansion fluid 5 can be injected into the front end of the chamber 3. The chamber 3 can be located on the longitudinal axis 9 as illustrated.

The implant 34 further includes a cap 8 that can be secured to the implant body 7, for instance to the front end 10 of the implant body 7, so as to close and seal the internal chamber 3. The cap 8 has an insertion portion 15 suitable to fit into the chamber 3 and a tip portion 16 that defines a tip portion of the implant 34. The implant body 7, the chamber 3, and the cap 8 are illustrated as distally spaced from each other along the longitudinal axis 9. The cap 8 can be fixed to the front end 10 of the implant body 7, e.g. by welding, to close and seal the chamber 3.

Additionally, implant 34 includes an internal cavity 12 defined in the implant body 7 that extends longitudinally distal from the rear end 11 toward the front end 11, and terminates at a location spaced from the chamber 3 such that the cavity 12 is in longitudinal alignment with the internal chamber 3. The internal cavity 12 is configured to receive the energy emitter 36, which can be, for instance, an electromagnetic radiation emitter 14 (e.g., photoconductor) as illustrated in FIG. 2C or a heat emitter 17 (see FIGS. 4A-4B). As will be appreciated from the description below, the energy emitter 36 is configured to provide energy to the implant 34, thereby causing at least a portion of the implant body 7 to expand after implantation. In accordance with the illustrated embodiment, the internal chamber 3 defines an expandable portion 2 of the implant body 7 that is configured to expand after the energy emitter 36 has provided energy to the implant 34.

As illustrated in FIGS. 1A-2D, the internal surface 37 can be coated or otherwise covered by an energy absorbing member 4, which an be a layer of chromophore, for instance. The implant body 7 can be made from any suitable material, such as a polymeric material, e.g. PMMA which is transparent so that the implant body 7 can serve as a photoconductor and light diffuser at locations between the cavity 12 and the chamber 3. Accordingly, after the electromagnetic radiation emitter 14 applies light to the implant body 7, the light is conducted through the implant body 7 until it arrives at the internal surface 37.

The expansion fluid 5 can be in liquid form in a first or initial state. As illustrated in FIGS. 2B-C, the supply of energy 105 to the expandable portion 2 of the implant body 7 and to the expansion fluid 5 in the chamber 3 raises the temperature of the expansion fluid 5 to a sufficient level that causes the expansion fluid 5 to vaporize to a gas in a second state. It should thus be appreciated that the pressure of the biocompatible fluid increases when the liquid expansion fluid 5 vaporizes into a gas. The temperature increase of the implant body 7 and the increased pressure of the expansion fluid 5 due to vaporization cause a plastic expansion of the expandable portion 2 of the implant body 7. After energy from the energy emitter 26 is discontinued, the expansion fluid 5 subsequently cools and the expanded portion 2 of the implant body 7 will remain in its expanded state due to the plastic deformation of the implant body 7 (FIG. 2D). Thus, even though the expansion fluid 5 can condense to a liquid in a third state, the expandable portion 2 remains expanded due to plastic deformation.

Figure 3B:
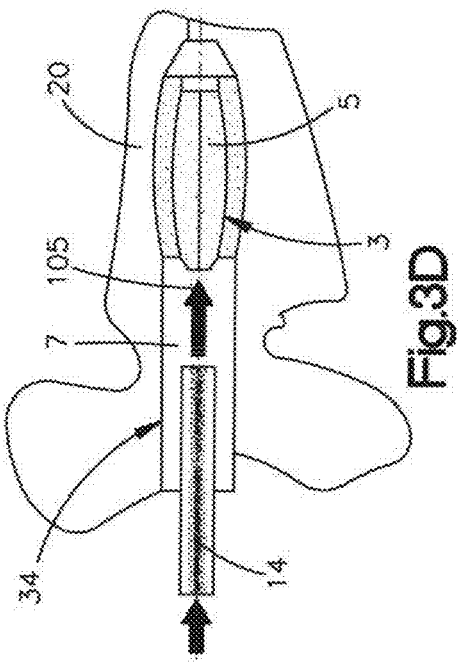
FIG. 3B is a sectional side elevation view similar to FIG. 3A, but showing an electromagnetic radiation emitter operably coupled to the implant.

Referring to FIGS. 3A-3G, the implant system 1 can be configured to fix the implant 34 in an underlying bone. For instance, a method of stabilizing a damaged vertebral body 13 with the implant system 1 can comprise the following steps:
  i) producing a cavity 20 in a vertebral body 13 to be treated;
  ii) inserting the implant body 7 in its unexpanded state into the cavity 20 (FIG. 3A);
  iii) inserting an energy emitter 36, for instance in the form of a photoconductor 14, into to the implant body 7, wherein the photoconductor 14 is connected to an energy source, e.g. a laser (FIG. 3B);

iv) supplying energy emitted by the energy emitter 36 to increase the temperature of the expansion fluid 5 and thereby the internal vapour pressure in the one or more chambers 3 of the implant 34 until the implant 34 achieves its expanded state (FIGS. 3C-3F); and v) removing the energy emitter from the implant body 7 (FIG. 3G).

Referring now to FIGS. 4A-B, the cavity 12 can extend longitudinally distal or forward from the rear portion 11 toward the front portion 10, and terminates at a location adjacent the tip portion 16. The tip portion 16 is illustrated as integral with the implant body 7. The implant body 7 defines a plurality of internal surfaces 37 that define a corresponding plurality of internal chambers 3. The chambers 3 can define any size and shape as desired, and can be the same or different size and shape with respect to one or more, up to all, of the other chambers 3. The chambers 3 are illustrated as round, e.g., spherical or elliptical, and can be offset with respect to the longitudinal axis 9. It can also be said that the chambers 3 are shaped as a plurality of bubbles integrated or captured in a peripheral wall 25 of the implant body 7. The peripheral wall 25 is disposed outward from the cavity 12 with respect to the central axis 9, and aligned with the cavity 12 along a transverse or radial direction that is angularly offset, for instance perpendicular, with respect to the longitudinal axis 9. Thus, it can be said that the peripheral wall 25 surrounds or substantially surrounds the cavity 12.

The chambers 3 are distributed along the peripheral wall 25. The chambers 3 therefore define an expandable portion 2 extending over substantially the entire length of the implant body 7. As illustrated in FIG. 4B, the cavity is configured to receive the energy emitter 36, which is illustrated as an electric heater 17 inserted in the cavity 12. It can be appreciated that a portion of the implant 34 can be devoid of chambers 3 at a region that does not form part of the expandable portion 2, and that the implant 34 can thus define a plurality of expandable portions 2, or at least one expandable portion. The energy emitter 36 can be configured as a heater 17 configured to provide heat to the expansion fluid 5 that is disposed in the chambers 3, thereby causing the fluid to vaporize from a liquid to a gas and expand the expandable portion 2 in the manner described above.

Figure 5A:
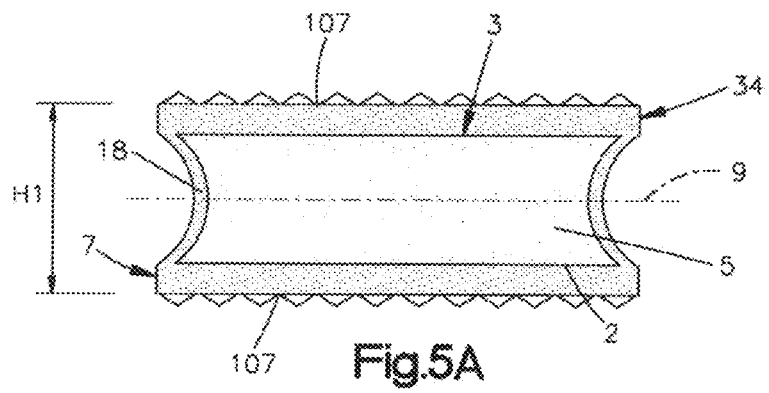
FIG. 5A is a sectional side elevation view of an expandable implant similar to the expandable implant illustrated in FIG. 4A, but constructed in accordance with another embodiment, the implant shown in an unexpanded state.
Figure 5B:
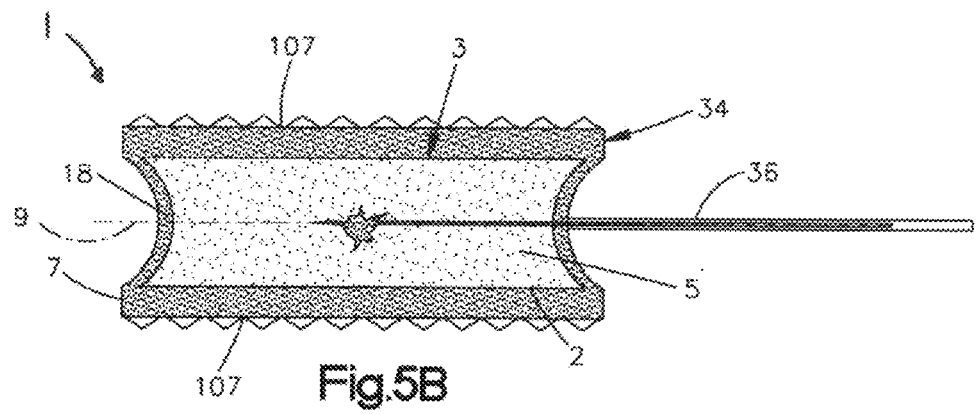
FIG. 5B is a sectional side elevation view of an implant system including the expandable implant illustrated in FIG. 5A and an energy emitter coupled to the implant.
Figure 5C:
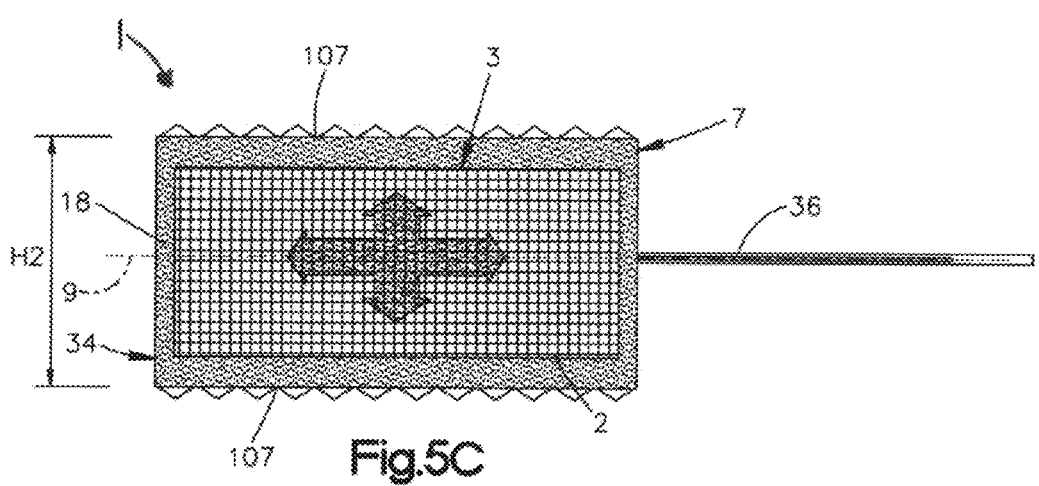
FIG. 5C is a sectional side elevation view of the implant system illustrated in FIG. 5B, showing the implant in an expanded configuration.
Figure 6A:
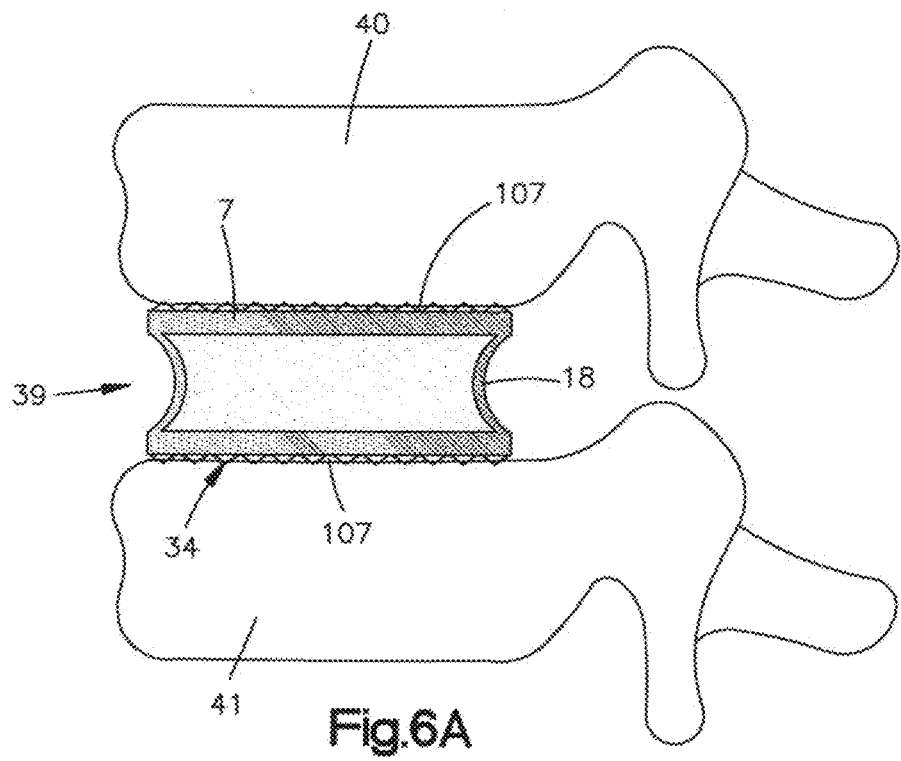
FIG. 6A is a side elevation view of the implant illustrated in FIG. 5A implanted into an intervertebral space in the unexpanded configuration.
Figure 6B:
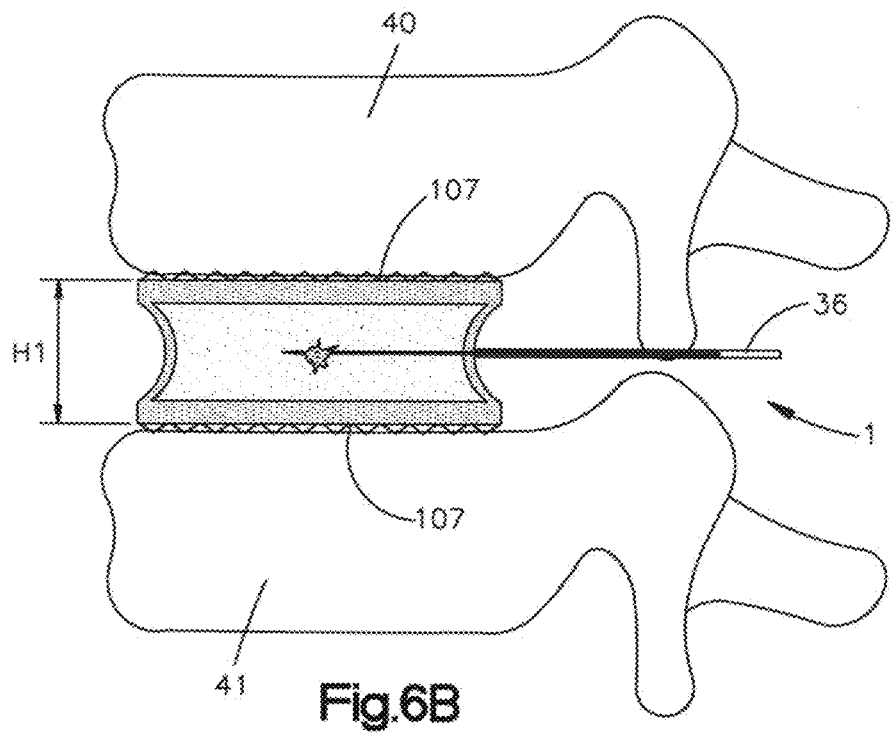
FIG. 6B is a side elevation view of the implant system illustrated in FIG. 5B implanted into the intervertebral space illustrated in FIG. 6A.

Referring now to FIGS. 5A-5C, the implant body 7 can be shaped substantially as a cuboid having opposing outer walls 18 spaced along the longitudinal axis 9 that are concavely curved toward each other when the implant 34 is in a first or unexpanded state. During application of energy in the form of heat, for example, provided by the energy emitter 36, the expansion fluid 5 vaporizes, and the internal pressure in the chamber 3 thereby increases. The pressure increase causes the concavely curved peripheral walls 18 to bulge outwardly so that a second expanded state of the implant 34 is achieved wherein the peripheral wall 18 is substantially planar, or more planar than when the implant 34 is in its first unexpanded state. Thus, the expandable portion of the implant body 7 expands from a first state having a first height H1 between opposed bone engaging surfaces 107 to a second state having a second height H2 between the opposed bone engaging surfaces 107 that is greater than the first height H1. In the second state, the planar peripheral walls 18 have a greater resistance to deformation.

Referring to FIGS. 6A-6D, the implant 34 illustrated in FIGS. 5A-5C can be configured as an intervertebral implant, and inserted into a disc space 39 disposed between a pair of adjacent vertebrae 40 and 41, such that the bone engaging surfaces 107 engage respective vertebral endplates. The implant 34 can be expanded as described above, such that the implant body 7 defines a first height H1 when the implant 34 is unexpanded, and a second height H2 greater than the first height H1 after the implant 34 has been expanded, thus providing height restoration to the intervertebral disc space 39.

Figure 7A:
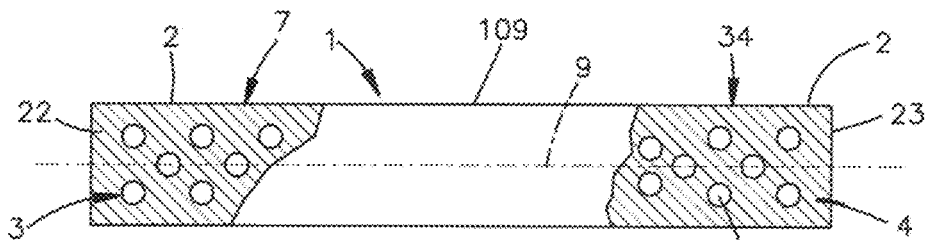
FIG. 7A is a sectional side elevation view of an expandable implant constructed in accordance with another embodiment, showing the implant in an unexpanded configuration.
Figure 7B:
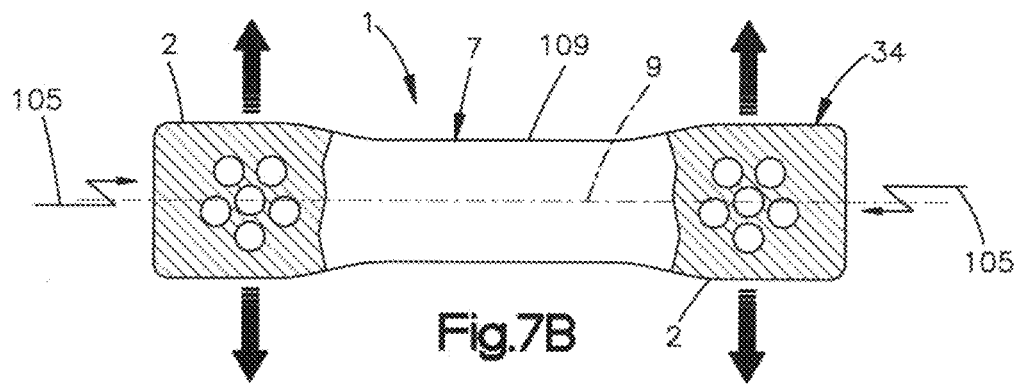
FIG. 7B is a sectional side elevation view of the expandable implant illustrated in FIG. 7A, shown in an expanded configuration.

Referring now to FIGS. 7A-7B, the chambers 3 can be shaped as bubbles integrated in the opposed first and second end portions 22 and 23, respectively, spaced along the longitudinal axis 9, that define corresponding expandable portions of the implant body 7. The implant body 7 defines a middle portion 109 that is disposed longitudinally between the end portions 22 and 23, and is devoid of chambers 3. It should be appreciated that the chambers 3 can alternatively be disposed in one of the first and second ends as desired. Thus, it can be said that the implant 34 includes a plurality of chambers disposed in at least one of the first and second ends of the implant body 7. The first and second chamber-containing ends 22 and 23 of the implant body 7 can be spaced by an air gap, and/or or by implant body material 7 that is devoid of chambers 3 or otherwise contains fewer chambers 3 than are disposed in the first and second end portions 22 and 23 of the implant body 7. Furthermore, the first and second end portions 22 and 23 of the implant body 7 can have a substantially equal number of chambers 3, or fewer or more chambers 3 than the other end portion. Otherwise stated, each of the first and second end portions 22 and 23 may be configured to expand substantially the same distance as the other end portion, or differently (e.g., greater or less) than the other end portion. It should be further appreciated that the middle portion 109 can be devoid of chambers 3 as illustrated, or can include one or more, such as a plurality of, chambers 3, such that the middle portion 109 can expand substantially equal to one or both of the end portions 22 and 23, or differently (e.g. greater or less) than one or both of the end portions 22 and 23.

The chambers 3 are illustrated as homogenously distributed in the first and second end portions 22 and 23, though it should be appreciated that the chambers 3 can be distributed irregularly as desired. In accordance with the illustrated embodiment, the chambers 3 cover substantially all of the cross-section of the implant body 7. The implant 34 can further include an energy absorbing member 4 disposed at one or both of the first and second end portions 22 and 23. As shown in FIG. 7B, when energy 105 is supplied to the energy absorbing member 4, for instance via a laser or alternative energy emitter, the first and second end portions 22, 23 expand in the manner described above in a direction transverse to the longitudinal axis 9, thereby imparting a dog-bone shape to the implant body 7. An energy source can be inserted into the first end portion 22 in the manner described above, the second end portion 24 in the manner described above, or both end portions 22 and 24 if desired.

Figure 8:
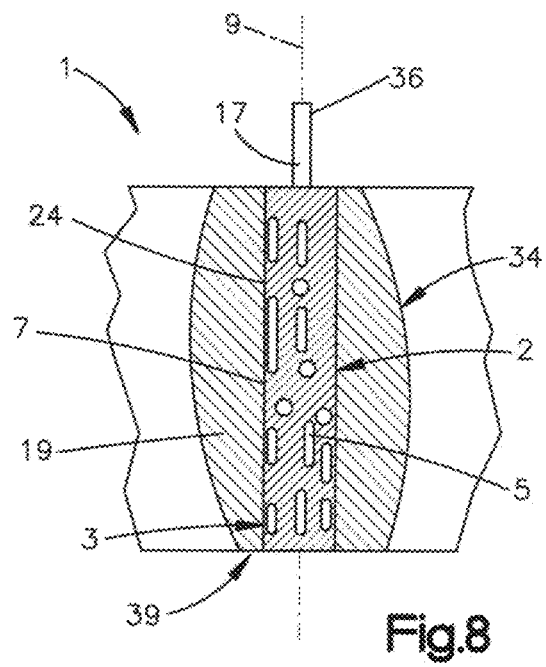
FIG. 8 is a sectional side elevation view of an expandable implant constructed in accordance with another embodiment.

Referring now to FIG. 8, the implant 34 can include plurality of chambers 3 that can be alternatively shaped as desired, and can be elongate, for instance along a direction substantially parallel to the longitudinal axis 9, so as to expand more in a direction transverse to the elongation of the chambers 3 (e.g., angularly offset or substantially transverse with respect to the longitudinal axis 9) than in a direction substantially parallel to the elongation of the chambers 3 (e.g., substantially parallel to the longitudinal axis 9). The implant system 1 can further include the energy emitter 36 as described above, and can further include an auxiliary implant such as an expandable, e.g., polymeric, intervertebral implant 19 that receives the implant 34. In this regard, it should be appreciated that the implant 34 provides an expansion force against the intervertebral implant 19, thereby causing the intervertebral implant 19 to expand within an intervertebral disc space 39. In particular, the intervertebral implant 19 defines an aperture 24 sized to receive the implant body 7, and in particular the expandable portion 2 of the implant body 7. The energy emitter 36, which can be provided as an electric heat emitter 17, applies energy in the form of heat to the expandable portion 2 of the implant body 7, thereby causing the chambers 3 to expand in the manner described above. After the chambers 3 have been subsequently cooled, the expandable portion 2 of implant body 7 can be removed from the intervertebral implant 19, which has plastically deformed.

Referring now to FIG. 9A, the implant 34 can be provided as an intervertebral implant 19 that includes an implant body 7 that defines an interior hollow void 43, and an expandable portion 2 disposed within the void 43. When the expandable portion 2 is in its unexpanded state, the expandable portion 2 can have a height less than that of the void 43. The implant body 7 further includes a first or upper guide portion 45a and a second or lower guide portion 45b, such that a first or upper channel 47a extends up from the void 43 and through the upper guide portion 45a, and a second or lower channel 47b extends down from the void 43 and through the lower guide portion 45b. The implant body 7 further includes a first or upper expandable part or slider member 26a and a second or lower expandable part slider member 26b that are at least partially disposed in the first and second channels 47a and 47b, respectively. When the implant 34 is in its unexpanded state, the first and second slider members 26a and 26b protrude into the inner hollow space and contact the expandable portion 2. Further, in the unexpanded state the slider members 26a-b do not project beyond the upper and lower surfaces of the upper and lower guide portions 45a-b, respectively.

As illustrated, the slider members 26a-b can substantially flush with the upper and lower surfaces of the guide portions 45a-b, though the slider members 26a-b can alternatively be recessed from, or can extend beyond, the upper and lower surfaces of the guide portions 45a-b as desired. The implant 34 can include at least one, such as a plurality of, chambers 3 distributed in the expandable portion 2 as desired. In order to expand the implant 34, energy is applied to the expandable portion 2 in the manner described above. During expansion of the expandable portion 2, the expandable portion 2 urges the slider members 26a-b outwardly away from the interior void 43 towards the adjacent upper and lower vertebral bodies, respectively. The slider members 26a-b define respective outer contact surfaces that include a plurality of teeth 29 so as to provide a primary anchoring of the expandable parts 26 and consequently of the intervertebral implant 34 in the vertebral bone. After the expansion fluid 5 cools off, the expanded portion 2 and the intervertebral implant 19 maintain the expanded state due to plastic deformation.

Referring now to FIG. 9B, it should be appreciated that the implant 34 illustrated in FIG. 9A can include any number of upper and lower slider members 26 as desired. For instance, as illustrated in FIG. 9B, the implant 34 includes two upper slider members 26a and three lower slider members 26b. Thus, the implant 34 can include at least one, such as a plurality of, upper slider members 26a, and at least one, such as a plurality of, lower slider members 26b. The implant 26 can include the same or different number of upper and lower slider members 26a and 26b.

Referring now to FIG. 10, the implant 34 can be provided as a bone fixation element which is in the form of a dowel including first and second opposed expandable parts or deflection members 51a and 51b, each plastically deformable. The deflection members extend down from a base portion 55 of the implant body 7. The implant 34 further includes an expandable portion 2 that is disposed in a space 53 disposed between the deflection members 51a and 51b. The implant 34 includes the expandable portion 2 arranged in an inner hollow space. The two expandable parts 26 form lateral walls limiting the inner hollow space. During expansion of the expandable portion 2, the expandable portion urges the deflection members 51a and 51b outward away from the longitudinal axis 9 so as to hinge about the base portion 55 towards the surrounding bone tissue so that the implant 34 can be anchored, for instance, in a hole in a bone like a dowel.

Referring now to FIGS. 11A-11C, the implant 34 can be configured as a bone plate having 111, such that the implant body 7 includes a bone plate portion 27, and defines an expandable portion 2 that extends out from the bone plate portion 27. The implant system 1 can further include at least one bone anchor 30, such as a plurality of bone anchors 30, illustrated as bone screws, that extend from the bone plate portion 27 and are configured to attach to underlying bone 6 to provide bone anchoring. The bone plate portion 27 can define a plurality of apertures configured to receive the bone anchors 30. The expandable portion 2 can provide primary bone anchoring, and the expandable portion 2 can include a plurality of chambers 3 as described above. The implant 34 can be inserted in its unexpanded state into a cavity 20 which is, for instance, caused by a defect of the bone. After fixation of the bone plate portion 27 to the underlying bone 6 via the bone anchors 30 the expandable portion 2 can be expanded by supplying energy from the energy emitter 36 to the expandable portion 2 in the manner described above.

Referring now to FIGS. 12A-12C, the implant body 7 can include a plurality of macroscopic structure or fibers 28 that extend out from an outer surface 57 of the expandable portion 2 and can encourage or facilitate new bone growth thereon. Such new bone growth can provide for an increased stability and reduced micro-motion between the interface between the implant 34 and the bone 6. The expandable portion 2 can have a shape during expansion that conforms to adapt to the shape of the bone defect or cavity 20. The expandable portion 2 can be resorbable if desired. Additionally, either or both of the bone plate portion 27 and the bone anchors 30 can be resorbable as desired. Suitable resorbable materials can include, for example, any of the family of polylactides (PLA) or polycaprolactones (PCL).

Figure 13A:
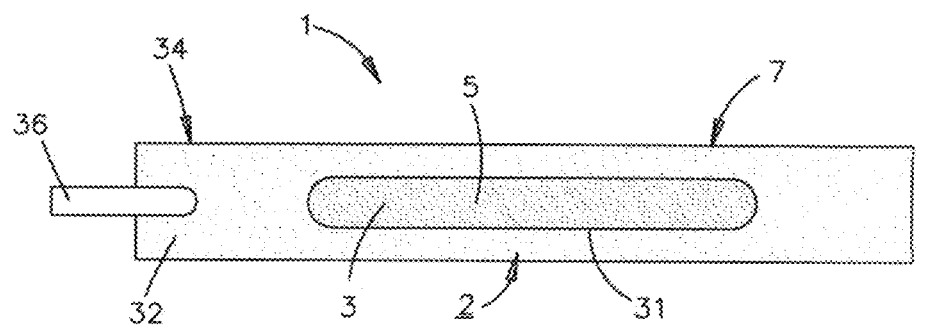
FIG. 13A is a sectional side elevation view of an implant having an implant body that defines a porous wrapping in accordance with another embodiment.
Figure 13B:
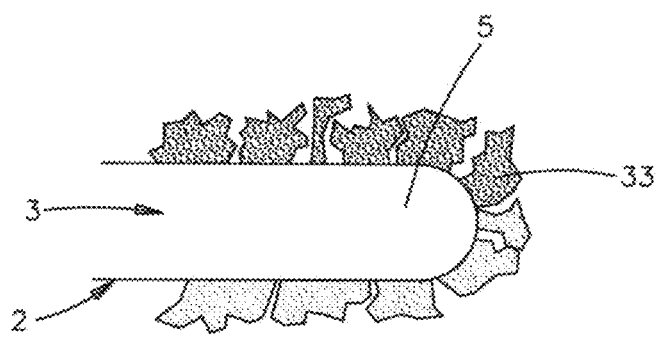
FIG. 13B is an enlarged sectional side elevation view of a portion of the implant illustrated in FIG. 13A.
Figure 13C:
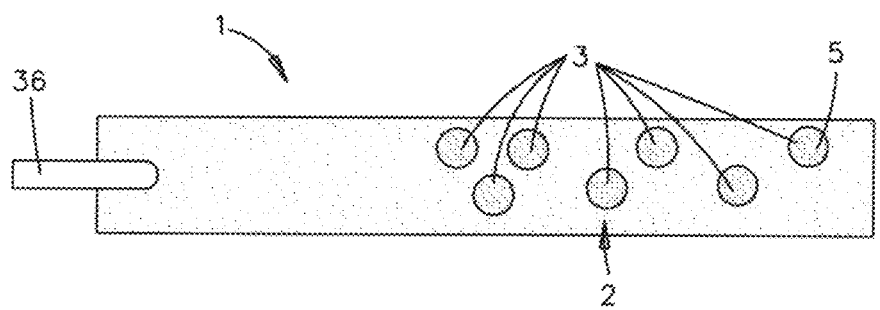
FIG. 13C is a sectional side elevation view of an implant similar to FIG. 13A, but including a plurality of chambers.

Referring now to FIGS. 13A-13B, the implant 34 includes an implant body 7 having an expandable portion 2 that can be made from PLLA (poly-L-lactide). The implant body 7 can define a wrapping 32 having open pores, and an oblong or elongate chamber 3 embedded in the wrapping 32. The implant 34 can include a single chamber 3 as illustrated in FIG. 13A, or a plurality of chambers 3 configured as bubbles (which can be substantially spherical or alternatively shaped when unexpanded) as illustrated in FIG. 13C. The chambers 3 are defined by an outer perimeter provided as a stiff envelope 31 that is filled with an expansion fluid 5, such as water. The envelope 31 softens during heating, and can again stiffen to provide stability when cooled. The envelope 31 can be made from of PLLA (poly-L-lactide). The wrapping 32 can be a spongy material with open pores or can be a coating 33 of particles or granules as illustrated in FIG. 13B. The particles or granules of the coating 33 can be made from calcium phosphate, e.g. TCP (tricalcium phosphate) or an apatite, e.g. HAP (hydroxylapatite). Thus, wrapping 32 can serve to provide a bone/implant interface that can encourage new bone growth and can provide additional anchorage of implant 34 to the bone into which the implant 34 is inserted.

Referring now to FIGS. 14A-14C, the implant 34 can be provided as a bone plate 111 including an implant body 7 that has a bone plate portion 27, and an implant body 7 extending out from the bone plate portion 27 that defines an expandable portion 2. The expandable portion 2 can be filled in a cavity 20 of the underlying bone 6. The bone plate 27 can be attached to the bone 6 via a plurality of bone anchors 30, e.g. bone screws, in the manner described above. The bone plate portion 27 prevents the implant 34 from swelling out of the cavity 20 when the expandable portion 2 expands. The expandable portion 2 can include at least one chamber 3 such as a plurality of chambers 3 defined by a closed outer perimeter provided as an envelope 31 made from PLLA (poly-L-lactide) that are embedded in a wrapping 32 consisting of a spongy material with open pores, in the manner described above. After the expandable portion 2 has been expanded and subsequently cooled, the implant 34 is configured to withstand greater amounts of mechanical strain. For instance, once the envelope 31 is cooled below its glass transition temperature, the polymer (e.g., PLLA) stiffens/hardens, and can thus withstand greater forces without undergoing deformation in the absence of internal pressurized gas.

Referring to FIGS. 15A-15D, an expandable implant system 50 in accordance with an alternative embodiment includes an expandable implant 54 and an expansion assembly 52 that includes an expansion device 56, an injection device 58, and an energy emitter 61. The implant 54 defines an internal chamber 59 that is configured to receive the expansion device 56 so as to operably couple the expansion assembly 52 to the implant 54 such that the expansion assembly 52 can expand the implant 54 during operation.

The implant 54 includes an implant body 60 that is longitudinally elongate along a central longitudinal axis 62. The implant body 60 can be cylindrical, or prismatic, or can define any alternative suitable shape as desired. The implant body 60 defines a first or front end 64 and a longitudinally opposed second or rear end 66. The implant body 60 defines the chamber 59, which extends longitudinally coaxially along the longitudinal axis 62. The chamber 59 defines an entrance section 68 with an orifice 70 disposed adjacent to an outer surface 72 of the implant body 60 located at the second end 66. The entrance section 68 is configured to receive the expansion device 56, thereby allowing insertion of the expansion device 56 into the chamber 59. The implant body 60 defines an expandable portion 74 that is in operative alignment with the chamber 59, which is disposed adjacent the entrance section 68 and coextensive with the entrance section 68. The chamber 59 is closed at or near the first end of the implant 54. The implant body 60 includes interior threads 76 that extend into the chamber 59 so as to define an engagement member configured to mate with a corresponding engagement member in the form of outer threads 78 of the expansion device 56.

The expansion device 56 includes a rod shaped sleeve 80 that is longitudinally elongate along a central longitudinal axis 82, which can be aligned with the central longitudinal axis 62 of the implant 54 when the expansion device 56 is inserted into the implant 54. The expansion device 56 defines a first or front end 84 and a second or rear end 86 that is longitudinally spaced from the front end 84. The sleeve 80 includes a substantially annular or tubular peripheral wall 88 that defines a central internal opening 90 that provides a pocket that is closed at the front end 84. The sleeve 80 defines at least one radial perforation 92, such as a plurality of radial perforations 92, that penetrates through the peripheral wall 88.

Accordingly, when the sleeve 80 is positioned in the chamber 59 of the implant 54, a biocompatible expansion fluid 94, such as a liquid or vapor, that is injected into the central opening 90 from the rear end 86 of the sleeve 80 can pass through the perforations 92 and penetrate into the chamber 59. The sleeve 80 defines a first or front portion 96 which can be closed by the front end 84 of the expansion device 56, and a longitudinally opposed second or rear portion 98 which includes outer threads 78 that are engageable with the inner threads 76 of the entrance section 68 of the chamber 59. Thus, by rotating or screwing the outer thread 78 of the sleeve 80 into the inner thread 76 in the entrance section 68, the sleeve 80 can be affixed to the implant 54 in a fluid tight manner. Accordingly, the expansion device 56 can inject the pressurized expansion fluid 94, such as a liquid or vapor, into the expandable portion 74 of the chamber 59. Additionally, the expansion device 56 can include a heating member 100, such as an electric heating member, that disposed on the sleeve 80 and configured to apply heat to the chamber and thus the injected biocompatible fluid. In accordance with one embodiment, the heating member 100 includes electrically conductive wiring 102 that extends through the rear portion 98 of the sleeve.

Referring now to FIG. 15B, the expansion device 56 includes a handle 104 coupled, directly or indirectly, to the sleeve 80. The energy emitter 61 can include an integrated power supply 106 (e.g. batteries) disposed in the handle 104. The power supply 106 is configured to supply electric energy to the conductive wiring 102, and thus the heating member 100. Thus, the expandable implant system 50 can include an energy emitter 61 that includes the heating member power supply 100 and 106 and is configured to supply emitted that increases the temperature of the expansion fluid 94. The expansion device 56 further includes an injection device 58 having a cannula 108, a cylinder 110 filled with the fluid 94 and a piston 112 displaceable in the cylinder 110. The cannula 108 is attached to front end of the cylinder 110 such that the cannula 108 can be inserted into the rear portion 98 of the sleeve, and into the central opening 90 of the sleeve 80. The piston 112 provides an actuator that can be pressed forward into the cylinder 110 towards the cannula 108 so as to provide a pressure that urges the expansion fluid 94 through the cannula 108 and into the central opening 90 of the sleeve 80.

After fixing the expansion device 56 to the implant 54, the heating member 100 is activated so as to deliver heat to the implant 54 until the implant 54 is sufficiently softened and plastically deformable. For instance, the temperature of the heating member 100 can be set to e level that is higher than the temperature of the implant body 60, such that the heat delivered from the heating member can cause the temperature of the implant body 60 to increase, thereby softening the implant body 60, which can be made from a polymeric material. Subsequently, the expansion fluid 94 can be injected into the central opening 90 of the sleeve 80, such that the expansion fluid 94 generates an expansion force in the chamber 59 that causes the implant 54 to expand after the implant body 60 has been softened. In this regard, it should be appreciated that the fluid 94 can be injected into the chamber 59 before or after the implant body 60 has been softened.

Injection of the expansion fluid 94 through the central internal opening 90 of the sleeve 80 causes the fluid 94 to travel through the perforations 92 and into the chamber 59 of the implant 54. In instances where the expansion fluid 94 is a liquid, the expansion fluid 94 can be heated and vaporized by the heat from the heating member 100, such that the expansion fluid 94 is transformed to a vapor that creates the expansion force against the implant body 60 in the chamber 59. The expansion force is sufficient to cause the implant body 60, for instance at the expandable portion 74, to expand from a first state to an expanded second state. The expansion force can therefore be created by heating the expansion fluid 94 until the expansion fluid 94 vaporizes so as to generate the expansion force.

Once the vaporized fluid has expanded the implant 54 to its desired shape, the heating member 100 can be turned off. The implant 54 is then allowed to cool, such that the temperature of the implant body 60 falls below its glass transition temperature, thereby hardening the implant body 60 to a rigid body. Cooling of the implant 54 further causes the pressured vapor to partially or fully condense or liquefy, thereby reducing the pressure in the internal chamber 59. After the implant 54 has cooled, the expansion device 56 can be removed and the implant 54 maintains its expanded state. Some or all of the injected fluid 94 can also be drained or otherwise removed from the implant chamber 59 as the expansion device 56 is removed, or after the expansion device 56 is removed.

While the expansion force is generated by vaporizing the fluid 94 which is provided as a liquid in one embodiment, it should be appreciated that the expansion force can be generated in accordance with alternative embodiments. For instance, the expansion force can be created by heating the fluid, but not causing the fluid to vaporize. For instance, the fluid can be injected as a vapor, such that subsequent heating of the vapor causes the vapor to expand, thereby generating the expansion force. In this regard, while the fluid is a heated vapor that applies the expansion force, it is recognized that other fluids, such as liquids, likewise expand when heated. Thus, the expansion force can be generated by heating the fluid 94, and in some embodiments the heat can cause the fluid to vaporize. Alternatively or additionally, the expansion force can be generated by the injection pressure of the fluid 94 that is delivered to the chamber 59 under pressure created by the injection device 58.

It should be appreciated that the implant 54 can assume any size and shape as desired. For instance, referring now to FIGS. 16A-16C, the implant body 60 of the implant 54 is illustrated as a substantially cuboid shape having that includes opposed outer walls 114 that are concavely curved when the implant 54 is in its unexpanded state. During application of heat and pressurized biocompatible fluid in the manner described above, the implant body 60 expands, which causes the opposed walls 114 to bulge outward so as to assume a substantially planar orientation when the implant 54 is in the expanded state, or a more planar configuration than when the implant 54 is in the unexpanded state. In the second state, the more planar peripheral walls 114 have a greater resistance to deformation.

Figure 16A:
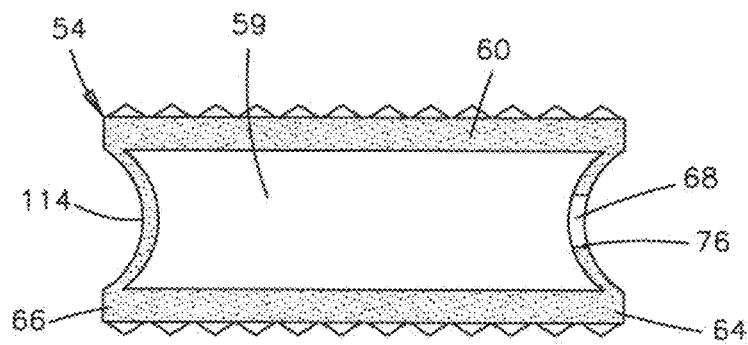
FIG. 16A is a sectional side elevation view of an expandable implant similar to the expandable implant illustrated in FIG. 15A, but constructed in accordance with another embodiment, the implant shown in an unexpanded state.
Figure 16B:
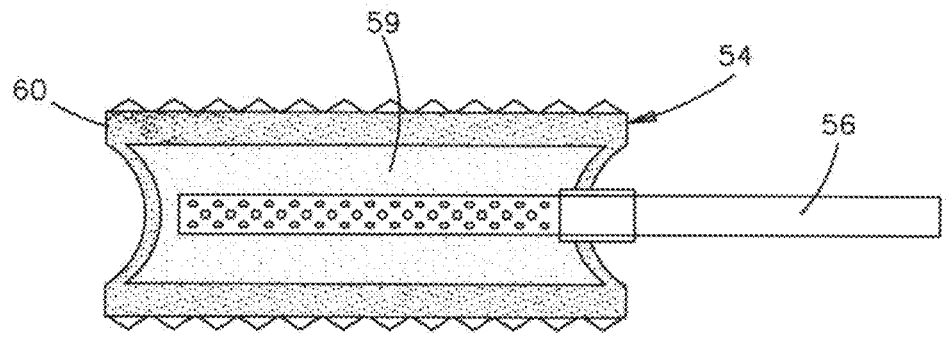
FIG. 16B is a sectional side elevation view of an implant system including the expandable implant illustrated in FIG. 16A and showing the expansion device operably coupled to the implant.
Figure 16C:
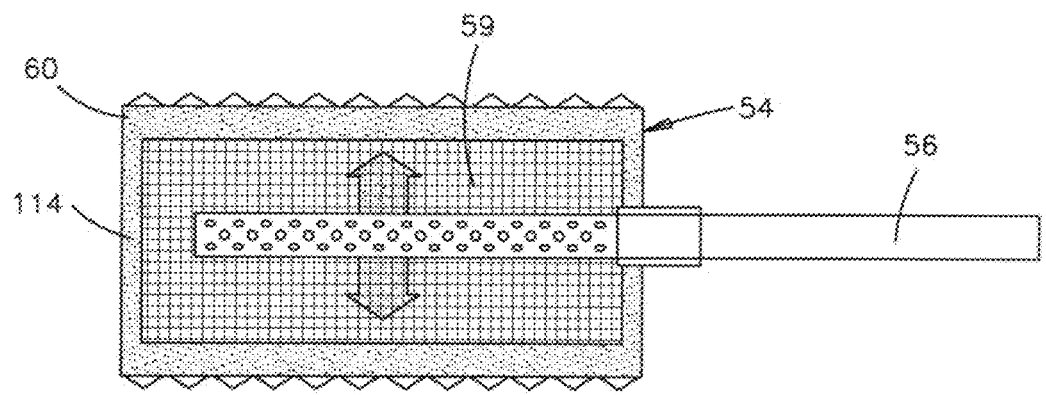
FIG. 16C is a sectional side elevation view of the implant system illustrated in FIG. 5B, showing the implant in an expanded configuration.
Figure 17A:
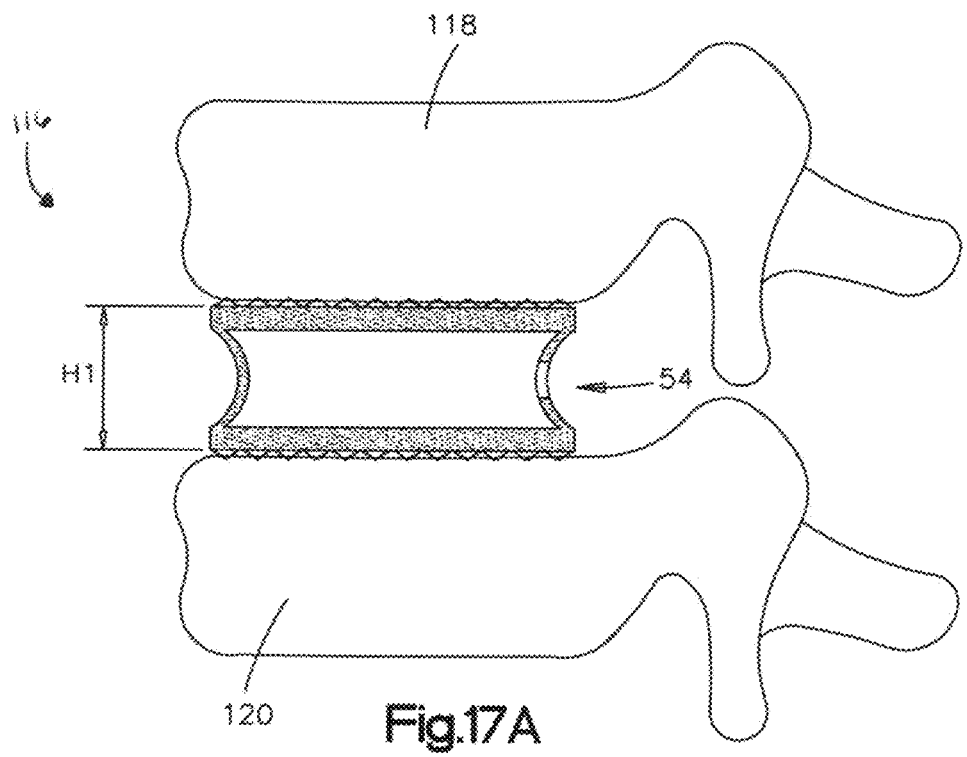
FIG. 17A is a side elevation view of the implant illustrated in FIG. 16A implanted into an intervertebral space in the unexpanded configuration.
Figure 17B:
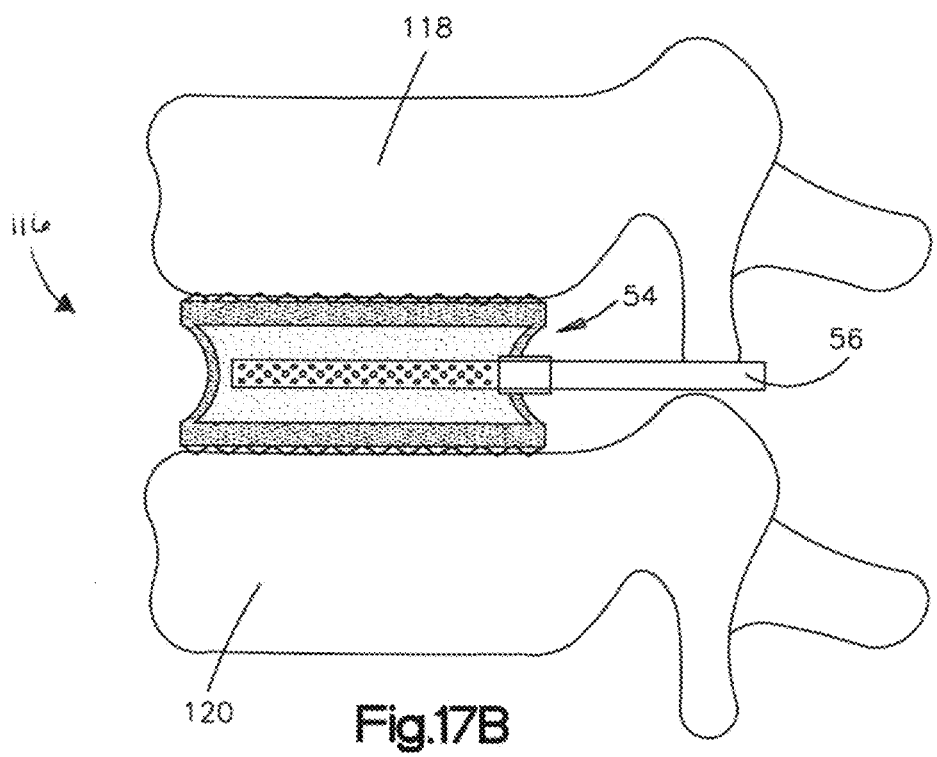
FIG. 17B is a side elevation view of the implant system illustrated in FIG. 16B implanted into the intervertebral space illustrated in FIG. 17A.
Figure 17C:
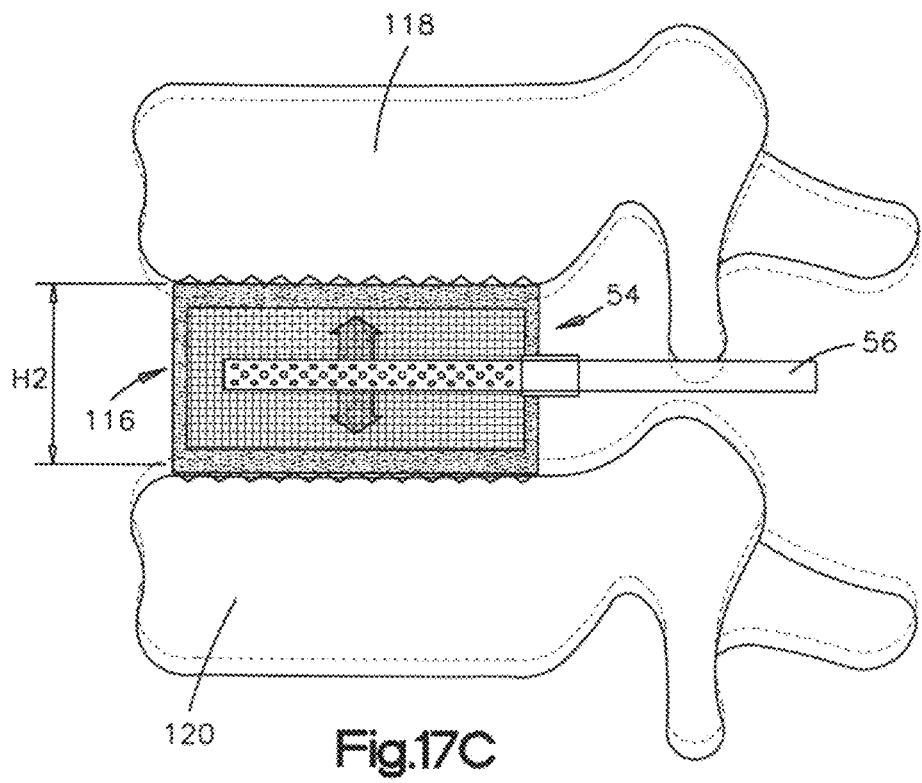
FIG. 17C is a side elevation view of the implant system illustrated in FIG. 17B, showing the implant in the expanded configuration.
Figure 17D:
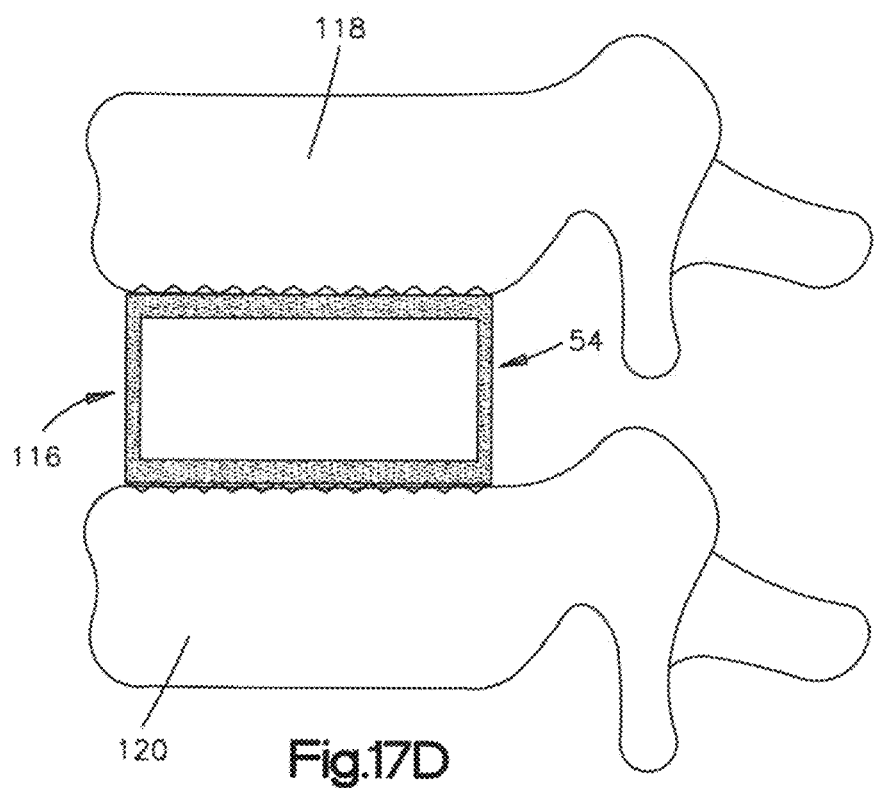
FIG. 17D is a side elevation view of the implant illustrated in FIG. 17C, whereby the energy emitter has been removed from the implant.

FIGS. 17A-17D illustrate an application of the embodiment of the implant 54 according to FIGS. 16A-16C as an intervertebral implant inserted into a disc space 116 disposed between a pair of adjacent vertebrae 118 and 120. The implant 54 can be expanded as described above, such that the implant body 60 defines a first height H1 when the implant 54 is unexpanded, and a second height H2 greater than the first height H1 after the implant 54 has been expanded, thus providing height restoration to the intervertebral disc space 116.

It should be appreciated that a bone fixation kit can be provided having components from one or more embodiments described herein. For instance, the bone fixation kit can include an implant having an implant body that defines a volume. The implant body defines at least one chamber that is configured to retain an expansion fluid at a pressure. The kit can further include an energy emitter configured to apply energy to the implant so as to deliver heat to the implant body. The applied energy causes the pressure of the expansion fluid to increases inside the at least one chamber so as to cause an expandable portion of the implant body to expand.

Although various embodiments have been described in detail, it should be understood that various changes, substitutions, and alterations can be made herein without departing from the spirit and scope of the invention, for instance as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the present disclosure, processes, machines, manufacture, composition of matter, means, methods, or steps, presently existing or later to be developed that perform substantially the same function or achieve substantially the same result as the corresponding embodiments described herein may be utilized.

The invention claimed is:

1. An implant comprising:
an implant body defining a central longitudinal axis and having a front end and a rear end, the rear end longitudinally spaced from the front end along the central longitudinal axis, the implant body having a total volume, the implant body defining at least one chamber disposed in an expandable portion of the implant body, the at least one chamber having a volume less than the total volume, and the implant body further defining a cavity sized and shaped to receive an energy emitter, the cavity extending longitudinally distal from the rear end toward the front end;
wherein the implant body is elongate along the central longitudinal axis in an initial state;
wherein the expandable portion comprises a polymeric material and has an expanded state;
wherein in the expanded state the at least one chamber is closed and contains a heated, and at least partially vaporized expansion fluid, and wherein the polymeric material of the expandable portion is heated to above its glass transition temperature and is plastically deformed;
wherein the volume of the expandable portion in the expanded state is greater than the volume of the expandable portion in the initial state;
wherein in the expanded state, the fluid exerts a vapor pressure on the at least one closed chamber; and,
wherein the expandable portion is adapted to maintain the expanded state volume below the glass transition temperature of the polymeric material and in the absence of the vapor pressure.

2. The implant according to claim 1, wherein the expansion fluid is disposed in the at least one chamber at the initial state.

3. The implant according to claim 1, wherein the expansion fluid inside the at least one chamber is a liquid at the initial state.

4. The implant according to claim 3, wherein the liquid is a composition based on polar molecules.

5. The implant according to claim 4, wherein the composition comprises liquid water or an aqueous solution.

6. The implant according to claim 1, wherein the expansion fluid inside the at least one chamber is a vapor at the initial state.

7. The implant according to claim 1, wherein the polymeric material is mixed with a calcium phosphate material.

8. The implant according to claim 1, wherein the polymeric material is transparent.

9. The implant according to claim 1, wherein the implant body is made from polymethylmethacrylate.

10. The implant according to claim 1, wherein the implant body is a substrate or core material for a calcium phosphate material.

11. The implant according to claim 1, further comprising an energy absorbing member configured to soften at least part of the implant body and increase the temperature of the expansion fluid in the at least one chamber.

12. The implant according to claim 11, wherein the energy absorbing member comprises a chromophore.

13. The implant according to claim 11, wherein the energy absorbing member is placed at an inner surface that at least partially defines the at least one chamber.

14. The implant according to claim 1, wherein the expandable portion of the implant body is configured to absorb energy.

15. The implant according to claim 1, wherein the expansion fluid is a colored energy receiver or absorber.

16. The implant according to claim 1, wherein the at least one chamber has a volume smaller than 100 mm$^3$ prior to expansion.

17. The implant according to claim 16, wherein the volume of the at least one chamber is smaller than 1 mm$^3$ prior to expansion.

18. The implant according to claim 1, wherein the total volume and a sum of the volumes of each chamber has a ratio in the range of 2:1 to 5:1.

19. The implant according to claim 1, wherein the at least one chamber is spaced from an outer surface of the implant body by at least 0.1 mm.

20. The implant according to claim 19, wherein the at least one chamber is spaced from the outer surface of the implant body of at least 0.2 mm.

21. The implant according to claim 1, wherein at the initial state, the volume of the at least one chamber is only partly filled with the expansion fluid.

22. The implant according to claim 21, wherein less than 50% of the volume of the at least one chambers is filled with the expansion fluid.

23. The implant according to claim 1, wherein the at least one chamber is open and configured to receive the expansion fluid in the initial state.

* * * * *